(12) United States Patent
Saric et al.

(10) Patent No.: US 11,299,453 B2
(45) Date of Patent: Apr. 12, 2022

(54) COMPOUNDS FOR USE IN THE ELIMINATION OF PLURIPOTENT STEM CELLS

(71) Applicant: Universität zu Köln, Cologne (DE)

(72) Inventors: Tomo Saric, Pulheim (DE); Albrecht Berkessel, Erftstadt (DE); Karsten Burkert, Cologne (DE); Jürgen Hescheler, Cologne (DE)

(73) Assignee: Universität zu Köln, Cologne (DE)

( * ) Notice: Subject to any disclaimer, the term of this patent is extended or adjusted under 35 U.S.C. 154(b) by 11 days.

(21) Appl. No.: 16/761,172

(22) PCT Filed: Nov. 6, 2018

(86) PCT No.: PCT/EP2018/080325
§ 371 (c)(1),
(2) Date: May 1, 2020

(87) PCT Pub. No.: WO2019/086707
PCT Pub. Date: May 9, 2019

(65) Prior Publication Data
US 2020/0339502 A1    Oct. 29, 2020

(30) Foreign Application Priority Data
Nov. 6, 2017 (EP) .................................... 17200161

(51) Int. Cl.
| | | |
|---|---|---|
| *C07C 215/64* | (2006.01) |
| *C07D 209/08* | (2006.01) |
| *C07D 209/14* | (2006.01) |
| *C07D 333/20* | (2006.01) |
| *C12N 5/077* | (2010.01) |

(52) U.S. Cl.
CPC .......... *C07C 215/64* (2013.01); *C07D 209/08* (2013.01); *C07D 209/14* (2013.01); *C07D 333/20* (2013.01); *C12N 5/0657* (2013.01); *C07C 2601/14* (2017.05); *C12N 2501/999* (2013.01); *C12N 2506/02* (2013.01); *C12N 2506/45* (2013.01)

(58) Field of Classification Search
None
See application file for complete search history.

(56) References Cited

FOREIGN PATENT DOCUMENTS

| | | |
|---|---|---|
| EP | 2415862 A1 | 2/2012 |
| WO | WO 2013/175474 A2 | 11/2013 |
| WO | WO 2015/112581 A1 | 7/2015 |

OTHER PUBLICATIONS

International Search Report dated Jan. 4, 2019 from corresponding International Application No. PCT/EP2018/080325.
European Search Report dated May 22, 2018 from corresponding European Application No. EP 17 20 0161.

(Continued)

*Primary Examiner* — Clinton A Brooks
(74) *Attorney, Agent, or Firm* — Davidson, Davidson & Kappel, LLC

(57) ABSTRACT

The present invention relates to a method of reducing the number or percentage of pluripotent stem cells or of enriching differentiating or differentiated cells in a cell population comprising pluripotent stem cells and differentiating cells or differentiated cells derived from the pluripotent stem cells, the method comprising the step of contacting the cell population with a compound according to the general formula (1).

19 Claims, 8 Drawing Sheets

(56) References Cited

OTHER PUBLICATIONS

Figure 1:
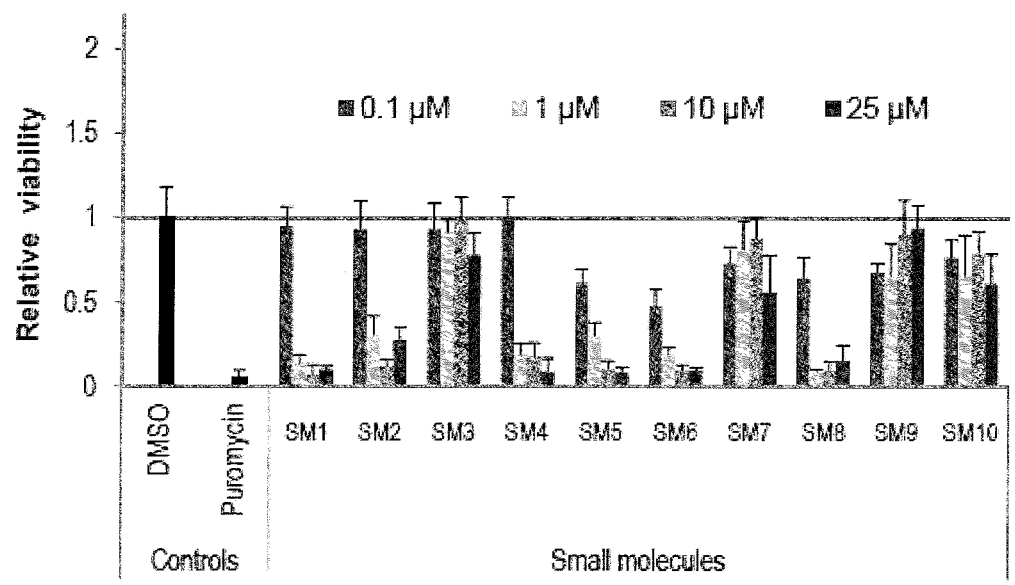

Adao et al. "Synthesis, Characterization, and Application of Vanadium—Salan Complexes in Oxygen Transfer Reactions" Inorganic Chemistry, vol. 48, No. 8, Apr. 20, 2009; pp. 3542-3561.
Berkessel et al. "A Practical and Versatile Access to Dihydrosalen (Salalen) Ligands: Highly Enantioselective Titanium In Situ Catalysts for Asymmetric Epoxidation with Aqueous Hydrogen Peroxide" Advaced Synthesis & Catalysis, vol. 349, Oct. 19, 2007; pp. 2385-2391.
Jimenez et al. "Synthesis of highly hindered polyanionic chelating ligands" Tetrahedron, vol. 61, No. 16, Apr. 18, 2005; pp. 3933-3938.
Dragoun et al. "Metal-free salan-type compound induces apoptosis and overcomes multidrug resistance in leukemic and lymphoma cells in vitro" Journal of Cancer Research and Clinical Oncology, vol. 144, No. 4, Apr. 2018; pp. 685-695.
European Written Opinion dated May 22, 2018 from corresponding European Application No. EP 17 20 0161.
International Written Opinion dated Jan. 4, 2019 from corresponding International Application No. PCT/EP2018/080325.

a)

b)

a)

b)

c)

COMPOUNDS FOR USE IN THE ELIMINATION OF PLURIPOTENT STEM CELLS

This application is a U.S. national phase application under 35 U.S.C. of § 371 of International Application No. PCT/EP2018/080325, Nov. 6, 2018, which claims priority of European Patent Application No. EP 17200161.27, filed Nov. 6, 2017, the disclosures of which are hereby incorporated by reference herein.

The present invention relates to the chemical ablation of undifferentiated cells in pluripotent stem cell-derived populations, and particularly to compounds able to selectively eliminate pluripotent stem cells in differentiated cell preparations.

Heart failure is one of the leading causes of worldwide morbidity, partially due to the limited capacity of cardiomyocytes (CMs) for self-regeneration. The generation of cardiomyocytes from pluripotent stem cells (PSCs) holds great promise in cardiac cell therapies. Of particular interest is the generation of induced pluripotent stem cells (iPSCs) by reprogramming fibroblasts to stem-like cells, thus evading ethical concerns in view of embryonic stem cells (ESCs). However, a fundamental obstacle in the use of pluripotent stem cell-derived cardiomyocytes (PSC-CMs) is the risk of undifferentiated pluripotent stem cells that remain in the population of differentiated cells forming tumours. This problem is due to an incomplete in vitro differentiation from pluripotent stem cells to cardiomyocytes, since a cell population of pure differentiated cardiomyocytes cannot be achieved in any of the current protocols. Therefore, it is crucial to eliminate undifferentiated pluripotent stem cells for a safe and successful application of pluripotent stem cell-derived cardiomyocytes in the clinic.

Various strategies have been developed for the elimination of pluripotent stem cells utilizing transgenic, immunologic and chemical approaches as well as biophysical techniques. While genetic manipulations are effective but raise safety concerns, pluripotent stem cell ablation by immunologic targeting is safe but less efficient because single-cell dissociation is required. Parr, C. J. et al. describe in Scientific Reports, vol 6, p. 32532, 2016, a method in which immunologic targeting of pluripotent stem cells using "microRNA-302 switch" allowed for a highly sensitive identification of undifferentiated cells as well as inhibition of teratoma formation after injection of microRNA-302-switch-sorted cells into mice. Further, a combination with a puromycin selection circuit allowed automated elimination of pluripotent stem cells without sorting. However, the applicability of these techniques in an up-scaled process generating billions of cardiomyocytes that will be needed for therapeutic applications will have to be demonstrated.

In this regard, the most promising strategy is the chemical ablation of undifferentiated cells in pluripotent stem cell-derived populations using small molecules such as toxins. The absence of genetic manipulations or single-cell dissociation makes this approach a save, fast, simple and inexpensive way to selectively kill pluripotent stem cells and enrich cardiomyocytes in the differentiation culture. WO 2013/175474 A2 for example describes a pluripotent cell-specific inhibitor (PluriSIn) for the chemical elimination of pluripotent stem cells. Exposure for 48 hours successfully removed human pluripotent stem cells from the culture and prevented teratoma formation after transplanting 1 million cells into immunodeficient mice. Nonetheless, not all studies could reproduce the elimination of pluripotent stem cells with the compound PluriSIn #1. Therefore, there remain obstacles for the utilization of PluriSIn #1 for the selective elimination of pluripotent stem cells.

On the other hand, WO 2014/118799 discloses chiral salicylic diamines as highly efficient homogeneous catalysts. Further, CN 101172955 A discloses chiral salicylic diamines as selective inhibitors of cancer cell growth but does not disclose a hint to a further use of the compounds.

Therefore, the object underlying the present invention was to provide compounds that allow for a selective elimination of pluripotent stem cells.

The problem is solved by a method of reducing the number or percentage of pluripotent stem cells or of enriching differentiating or differentiated cells in a cell population comprising pluripotent stem cells and differentiating cells or differentiated cells derived from the pluripotent stem cells, the method comprising the step of contacting the cell population with a compound according to the following general formula (1) and/or racemates, enantiomers, stereoisomers, solvates, hydrates or salts thereof:

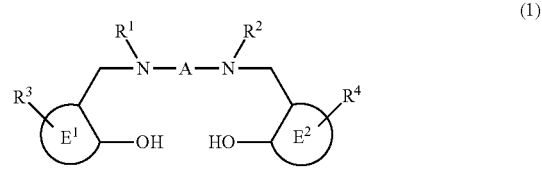

(1)

wherein:

$R^1$, $R^2$ the same or independent from each other are hydrogen or represent a double bond from the nitrogen atom to the adjacent non-cyclic carbon atom;

$R^3$, $R^4$ are the same or independently from each other selected from the group comprising hydrogen, linear or branched $C_1$-$C_8$-alkyl, $C_2$-$C_8$-alkenyl, $C_3$-$C_8$-cycloalkyl, $C_6$-$C_{10}$-aryl, $C_1$-$C_8$-alkoxy and halogen;

$E^1$, $E^2$ are the same or independent from each other a 5- or 6-membered aromatic or heteroaromatic ring selected from the group comprising thiophenyl, pyrrolyl, pyridyl and phenyl;

A is selected from the group of structural elements of formulas (2) and (3):

(2)

(3)

wherein:

B is selected from the group comprising $C_3$-$C_8$-cycloalkyl, $C_3$-$C_8$-heterocycloalkyl, $C_6$-$C_{10}$-aryl and $C_5$-$C_{10}$-heteroaryl;

Z is the same or independently from each other selected from the group comprising —$CH_2$—, —CHR'—, O, S, NH, NR';

R' is the same or independently from each other selected from the group comprising hydrogen, $C_1$-$C_8$-alkyl, $C_2$-$C_8$-alkenyl, $C_3$-$C_8$-cycloalkyl and $C_6$-$C_{10}$-aryl;

n, m are the same or independent from each other 0, 1 or 2;

p is 1, 2, 3, 4 or 5.

The compounds of formula (1), particularly the compounds of formula (4), are capable of selectively eliminating pluripotent stem cells from their differentiated derivatives. The compounds exhibited high cytotoxicity to murine and human pluripotent stem cells but not to cardiomyocytes derived from these. The compounds of formula (1), and particularly the compounds of formula (4), are usable for the elimination of pluripotent stem cells from differentiating derivatives of pluripotent stem cells that contain cardiomyocytes, either in unpurified or pre-purified form. A further advantage of the compounds of formula (1) is that the compounds show significantly higher pluripotent stem cell-specific cytotoxic activity in comparison to known small molecules such as PluriSIn #1. The compounds of formula (1) thus provide an efficient agent for the elimination of pluripotent stem cells from cardiomyocyte preparations, thereby decreasing the risks upon transplantation of the derived cardiomyocytes.

Advantageously, the compounds of formula (1) have no effect on the differentiation or differentiation potential of the cells in the population. The compounds of formula (1) thus provide a pluripotent stem cell-specific inhibitor. The method thus preferably is a method of eliminating pluripotent stem cells (PSCs), particularly induced pluripotent stem cells (iPSCs) or embryonic stem cells (ESCs) but also other pluripotent stem cell types such as parthenogenetic pluripotent stem cells (pgPSCs) and pluripotent stem cells derived by somatic cell nuclear transfer (SCNT) technology (scntPSCs), in a cell population comprising pluripotent stem cells and differentiating or differentiated cells derived from the pluripotent stem cells.

The term "alkyl" according to the invention is to be understood as meaning straight-chain or branched alkyl groups. The term "linear $C_1$-$C_8$-alkyl" as used herein refers to straight-chain groups having 1 to 8 carbon atoms. Linear $C_1$-$C_8$-alkyl groups may be selected from the group comprising methyl, ethyl, n-propyl, n-butyl, n-pentyl, n-hexyl, n-heptyl and n-octyl. The term "alkenyl" according to the invention is to be understood as meaning straight-chain or branched alkyl groups having at least one double bond between carbon atoms.

The term "$C_3$-$C_8$-cycloalkyl" according to the invention is to be understood as meaning a 3- to 8-membered saturated ring, and refers to the group comprising cyclopropyl, cyclobutyl, cyclopentyl, cyclohexyl, cycloheptyl and/or cyclooctyl. The term "$C_6$-$C_{10}$-aryl" according to the invention is to be understood as meaning a 6- to 10-membered aromatic ring, such as phenyl (Ph) and naphthyl. The term "$C_5$-$C_{10}$-heteroaryl" according to the invention is to be understood as meaning a 5- to 10-membered aromatic ring comprising at least one hetero atom, preferably selected from O, S and N. The term "halogen" according to the invention is to be understood as meaning fluorine, chlorine, bromine or iodine, preferably fluorine, chlorine or bromine.

The bridging element A may comprise 2, 3 or more carbon atoms or hetero atoms, but otherwise may vary in its structure. It has been found that the substitution pattern of the compounds of formula (1) is important, while the bridging element A may vary. Preferably, A may be a structural element of formula (2) being or comprising a cyclic structure, or A may be a linear structural element of formula (3).

Referring to the structural element of formula (3) —CHR'—(Z)$_p$— the element Z preferably may be a group —CHR'— and/or p preferably may be 1 or 2. R' preferably may be selected from hydrogen, $C_1$-$C_3$-alkyl or phenyl. In embodiments, A may be selected from —CH$_2$—CH$_2$—, —(CH$_2$)$_3$— or —(CHphenyl)$_2$-, preferably —CH$_2$—CH$_2$—.

Preferably, A is a structural element of formula (2) —(Z)$_n$—B—(Z)$_m$—. Referring to the structural element of formula (2) Z preferably may be a group —CH$_2$— and/or m and n preferably may be 0 or 1. Preferably, m and n are the same of 0 or 1. In embodiments, A is a structural element of formula (2) wherein n and m are 0. In embodiments of A being a structural element of formula (2) wherein n and m are 0, A is identical to B. In preferred embodiments, A or B is a 3- to 10-membered carbocyclic, heterocyclic, aromatic or heteroaromatic ring moiety selected from the group comprising $C_3$-$C_8$-cycloalkyl, $C_3$-$C_8$-heterocycloalkyl, $C_6$-$C_{10}$-aryl and $C_5$-$C_{10}$-heteroaryl. The ring moieties include bicyclic groups in which a 5- or 6-membered ring is fused to a further ring, such as a benzene ring. A ring moiety advantageously provides for the stability of the bridging element A.

The element A or B may be selected from the group comprising benzene, furan, tetrahydrofuran, thiophene, tetrahydropyran, pyrrole, pyrrolidine, imidazole, piperidine, piperazine, pyridine, pyrimidine or morpholine. Preferably, A or B may be a 5- or 6-membered carbocyclic, heterocyclic, aromatic or heteroaromatic ring. In preferred embodiments, A or B is a 5- or 6-membered carbocyclic ring selected from the group comprising cyclopentyl and/or cyclohexyl. In further embodiments, A or B may be a 6-membered heteroaromatic ring selected from the group consisting of pyridyl, pyridazyl, pyrimidyl and/or pyrazyl, or a 5-membered heteroaromatic ring selected from the group consisting of thiazolyl, oxazolyl, imidazolyl, pyrazolyl, thiophenyl, furyl and/or pyrrolyl.

The amine and imine groups, particularly diamine groups preferably are bound in a 1,2-, 1,3- or 1,4-fashion to a ring element A or B, particularly to a 5- or 6-membered carbocyclic, heterocyclic, aromatic or heteroaromatic ring. Preferably, the amine and imine groups, particularly diamine groups are bound in a 1,2-fashion. Most preferably, the element A is cyclohexyl and the diamine groups are bound in a 1,2-fashion.

The elements $E^1$ and $E^2$ are a 5- or 6-membered aromatic or heteroaromatic rings selected from thiophenyl, pyrrolyl, pyridyl and phenyl. Preferably, $E^1$ and $E^2$ are the same and selected from pyridyl or phenyl, particularly $E^1$ and $E^2$ are phenyl rings.

In preferred embodiments, the compound is a compound according to the following general formula (4) and/or racemates, enantiomers, stereoisomers, solvates, hydrates or salts thereof:

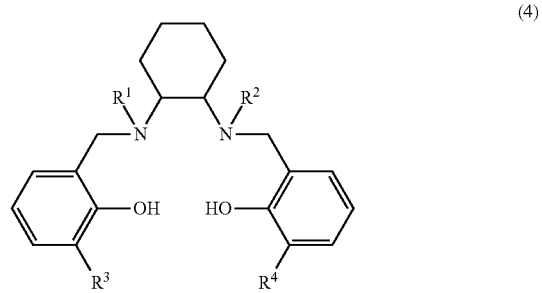

(4)

wherein:
$R^1$, $R^2$ the same or independent from each other are hydrogen or represent a double bond from the nitrogen atom to the adjacent non-cyclic carbon atom; and
$R^3$, $R^4$ are the same or independently from each other selected from the group comprising hydrogen, linear or branched $C_1$-$C_8$-alkyl, $C_2$-$C_8$-alkenyl, $C_3$-$C_8$-cycloalkyl and $C_6$-$C_{10}$-aryl.

The compounds of formula (4) advantageously demonstrated highly selective cytotoxicity against pluripotent stem cells.

The compounds of formula (1) may be denoted diamines. The compounds of formula (4), of formulas (5), (6) and (7), and of formulas (SM1) to (SM10), may be denoted salicylic diamines. $R^1$ and $R^2$, the same or independent from each other may represent a double bond from the nitrogen atom to the adjacent non-cyclic carbon atom, or a carbon-carbon bond to the adjacent non-cyclic carbon atom.

The compound of formula (1) and the compound of formula (4) comprise the substituents $R^1$ to $R^4$. It could be shown that compounds wherein $R^1$ and $R^2$ are hydrogen or represent a bond exhibited good toxicity to murine induced pluripotent stem cells. Preferably, at least one of $R^1$ and $R^2$ are hydrogen. In embodiments, $R^1$ and $R^2$ both are hydrogen. In embodiments, $R^3$ and $R^4$ are the same or independently from each other selected from the group comprising hydrogen, linear or branched $C_1$-$C_5$-alkyl, and phenyl. Preferred linear or branched $C_1$-$C_5$-alkyl groups are selected from methyl, ethyl and t-butyl. In preferred embodiments, $R^3$ and $R^4$ are the same, and selected from the group of hydrogen and phenyl.

In preferred embodiments, $R^1$ and $R^2$ are the same or independent from each other hydrogen or represent a double bond from the nitrogen atom to the adjacent non-cyclic carbon atom, and $R^3$ and $R^4$ are the same or independently from each other selected from the group comprising hydrogen, linear or branched $C_1$-$C_5$-alkyl, and phenyl. Preferably, at least one or both of $R^1$ and $R^2$ are hydrogen, and $R^3$ and $R^4$ are the same and selected from the group of hydrogen and phenyl (Ph).

In preferred embodiments, the compound is selected from the group of compounds according to formulas (5), (6) and (7) as indicated below and/or racemates, enantiomers, stereoisomers, solvates, hydrates or salts thereof:

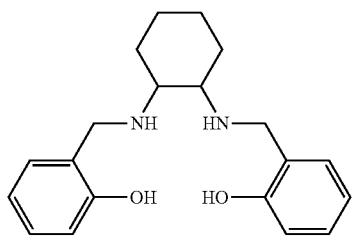

(5)

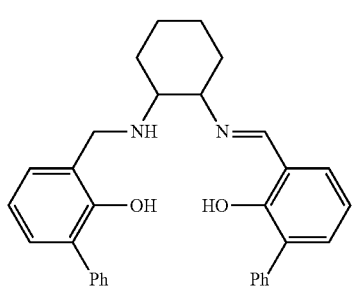

(6)

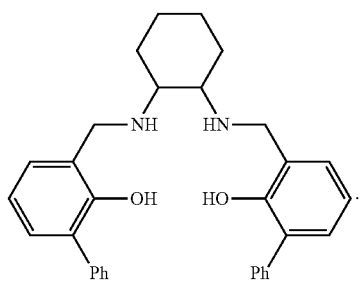

(7)

The compound of formula (6) illustrates that $R^2$ represents a double bond from the nitrogen atom to the adjacent non-cyclic carbon atom. Advantageously, a treatment with compounds of formulas (5), (6) and (7) eliminated pluripotent stem cells from a cell culture, while the physiology and functionality of differentiated cardiomyocytes were not permanently compromised. The compounds of formulas (1), (4), (5), (6) and (7) contain one or more asymmetric centres and may thus give rise to stereo isomers (configurational isomers). The present invention includes all such possible stereo isomers as well as their mixtures, and pharmaceutically acceptable salts thereof.

In embodiments, the compound is selected from the group of compounds according to formulas (SM1), (SM2), (SM4), (SM5), (SM6) and (SM8) as given as follows:

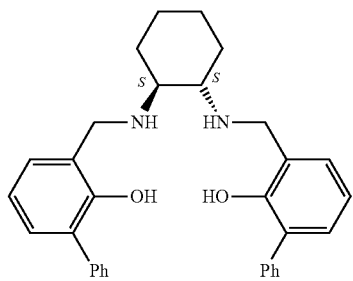

(SM1)

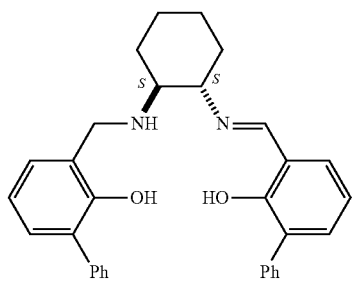

(SM2)

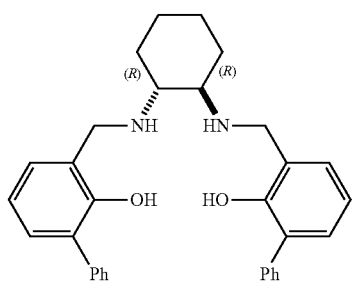

(SM4)

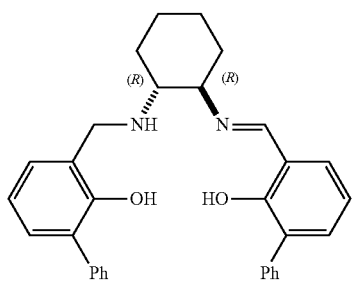
(SM5)

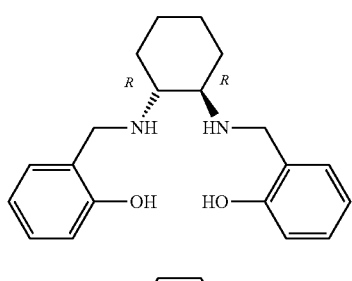
(SM6)

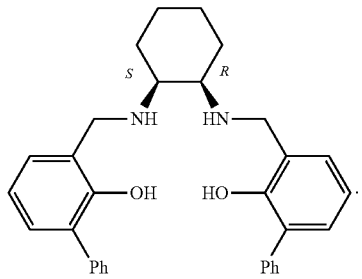
(SM8)

In preferred embodiments, the compound is selected from the group of compounds according to formulas (SM2), (SM6) and (SM8) as given as follows:

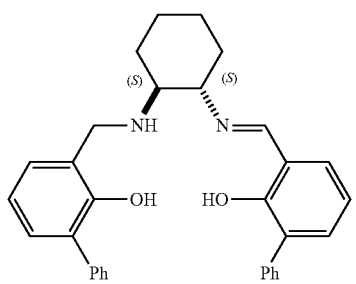
(SM1)

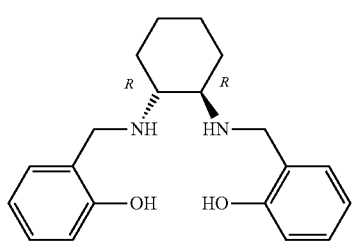
(SM6)

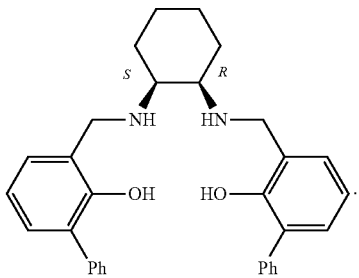
(SM8)

The compounds of formulas (SM6), (SM2) and (SM8) exhibited particular specific cytotoxicity towards pluripotent stem cells. The most preferred compound is the compound according to formula (SM6). The compound SM6 advantageously demonstrated a particular high selectivity for undifferentiated pluripotent stem cells. The compound SM6 further advantageously displayed a particularly high cytotoxic activity towards murine embryonic and induced pluripotent stem cells with an $IC_{50}$ value in a range from 0.1 to 0.5 μM and an $IC_{50}$ value of 1.9 μM towards human induced pluripotent stem cells, but was not toxic to and showed lowest side-effects on differentiated cardiomyocytes.

Unless specifically stated otherwise, compounds, groups or substituents denoted with Arabic numerals differ from compounds, groups or substituents denoted with Roman numerals or a combined naming of numerals and letters, that is, compounds, groups or substituents are different compounds, groups or substituents.

The compounds can be easily prepared at large scale in few synthetic steps from readily available commercial starting compounds. This advantageously enhances the potential applications for the pharmaceutical industries. The compounds may be usable in the form of solvates, hydrates, and salts such as pharmaceutically acceptable salts. The term "pharmaceutically acceptable salt" refers to salts prepared from pharmaceutically acceptable non-toxic bases or acids. A pharmaceutically acceptable salt can be conveniently prepared from pharmaceutically acceptable non-toxic bases, including inorganic bases and organic bases, organic anions, organic cations, halides or alkaline. The term pharmaceutically acceptable salt includes alkali metal salts and addition salts of free acids or free bases. Suitable pharmaceutically acceptable base addition salts include metallic salts and organic salts. Preferred salts derived from inorganic bases include ammonium, calcium, magnesium, potassium and sodium salts. Salts derived from pharmaceutically acceptable organic non-toxic bases include salts of primary, secondary, and tertiary amines.

The compounds of formula (1) and particularly the compounds of formula (4) are usable for the eradication of undifferentiated stem cells from specialised cell types. The compounds thereby can reduce the number or the percentage of pluripotent stem cells in a population of cells comprising pluripotent stem cells and differentiating cells or differentiated cells derived therefrom. The method allows for a selective elimination of pluripotent stem cells from differentiated populations of pluripotent stem cell derivatives, including cardiomyocytes but also other differentiated cell populations which are not negatively affected by the compounds according to the invention.

As used herein, the term "population" refers to a collection of more than one cell or cell type, typically a cell culture. As used herein, the term "differentiate" refers to the generation of a cell type that is more specialized than is the cell type from which it is derived. The term "differentiating or differentiated cells" therefore encompasses cells that are partially and terminally differentiated. The term "differentiating cells" particularly refers to cells being in the process of differentiation and maturation, while the term "differentiated cells" particularly refers to cells that have completed the process of differentiation and maturation. Differentiated cells derived from pluripotent stem cells are generally referred to as "PSC-derived cells". The differentiation may be determined by analyzing the cells for the presence of markers that identify pluripotent stem cells, such as OCT4, SSEA-4, TRA-1-81 and NANOG, or markers that are specifically expressed in specific types of differentiated cells, such as cardiac α-actinin in the heart cells, MAP2 in neuronal cells or albumin in hepatocytes. These and other markers may be detected by any method known in the art, including RT-PCR, immunohistochemistry, flow cytometry, ELISA and Western blotting.

Usually, a "pluripotent stem cell" is usable as the starting material for differentiation, particularly to cardiomyocytes. As used herein, the term "pluripotent" refers to cells that are capable of both proliferation and self-renewal in cell culture, and differentiation towards a variety of cell populations including cardiomyocytes. The pluripotent cells may be derived using any method known to those of skill in the art. In embodiments, the pluripotent stem cells (PSCs) are induced pluripotent stem cells (iPSCs) or embryonic stem cells (ESCs) or parthenogenetic pluripotent stem cells (pgPSCs) or pluripotent stem cells derived by somatic cell nuclear transfer (SCNT) technology (scntPSCs). In preferred embodiments, the pluripotent stem cells are human induced pluripotent stem cells (hiPSCs) or humen embryonic stem cells (hESCs). The term "induced pluripotent stem cells (iPSCs)" refers to a type of pluripotent stem cells artificially prepared from a non-pluripotent cell, e.g., a multipotent cell or terminally differentiated cell, through a process by which a differentiated cell reverts to a less specialized precursor or stem cell state.

The cells may be any species, and cells include both human cells and animal cells, and include murine cells or rat cells, for example for medical purposes. In embodiments the cells are mammalian cells, particularly primate cells, such as human cells. A pluripotent stem cell eliminating and cardiomyocyte preserving effect of the compounds could be observed on murine cells and also on human induced pluripotent stem cells. In preferred embodiments, the pluripotent stem cells are human cells.

Differentiating or differentiated cells are typically derived from pluripotent stem cells of various types such as ESCs, iPSC, pgPSCs, and may include such cells as cardiomyocytes, insulin-producing β-cells, smooth muscle cells, liver cells, as well as different types of neuronal cells, blood cells, retinal cells, and other cell types. In preferred embodiments, the differentiating or differentiated cells are cardiomyocytes. In embodiments, the cardiomyocyte subtypes are selected from the group of atrial (AM), ventricular (VM), and pacemaker (PM) cells.

The method comprises the step of contacting the cell population with a compound of formula (1). As used herein, the term "contacting" is intended to include incubating the cell and the compound together in vitro, such as by adding the compound to cells in culture. In other words, the cell population may be treated with a compound of formula (1). The step of contacting the cell population with a compound particularly may comprise incubating or culturing the cell population in a cell culture medium containing the compound. Such cell culture media generally are aqueous compositions containing inorganic and organic components for culturing cells. Usable media are commercially available. In other embodiments, cells can be contacted or treated with compounds in formulations other than cell culture and cell culture medium, for example cells in tissue constructs as well as cells in bioprinted 3D constructs. Further, the cells can be admixed with other therapeutic cell types, for example generated from other sources, and/or drugs, bioactive agents, biomaterials or nanomaterials.

The population of cells may be a cell culture. The cell culture may be a static or dynamic suspension culture, which can be a suspension of cell aggregates with or without carriers, or an adherent culture. The cell culture may be a small-scale culture such as in 96-well and 6-well plates, or larger plates or flasks, or may be a large-scale culture such as in spinner flasks, bioreactor vessels and other vessels. The method can be utilized in small scale or large scale cell cultures as required for the preclinical and clinical implementation. In other embodiments, the population of cells may be a tissue construct such as a tissue engineered 3-dimensional construct or cells in microfluidic devices or in a, so called, organ-on-a-chip devices. The population of cells may contain or may not contain other components, such as biomaterials, nanomaterials and bioactive molecules.

In embodiments, the step of contacting the cell population with a compound comprises incubating the cell population in a cell culture medium containing a compound according to general formula (1), preferably a compound of formulas (4) to (7), particularly of formulas (SM6), (SM2) and (SM8), in a range from ≥0.01 μM to ≤100 μM, preferably in a range from ≥0.05 μM to ≤10 μM, more preferably in a range from ≥0.05 μM to ≤2 μM. These concentrations were found to be sufficient to provide a cytotoxic activity towards pluripotent stem cells. Particularly it could be shown that the viability of mouse and human pluripotent stem cell-derived cardiomyocytes was not affected when being exposed to such concentration ranges, which on the other hand eliminated pluripotent stem cells. It could, for example, be shown that a two day-treatment of pluripotent stem cells with 10 μM of the compound SM6 resulted in the elimination of pluripotent stem cells but had no significant effect on the viability of cardiomyocytes under the same conditions.

The compounds are capable of selective elimination of pluripotent stem cells from their differentiated derivatives, such as of therapeutic interest. The compounds thus are usable in methods of reducing the number or percentage of pluripotent stem cells or in methods of enriching differentiating or differentiated cells in a cell population, depending on the use of the method.

The compounds of formula (1), and particularly the compounds of formula (4), advantageously are usable for enrichment of differentiated cells, such as cardiomyocytes or cardiomyocyte subtypes, from mixed populations of pluripotent stem cells and their derivatives. In embodiments, the method is a method for enriching cardiomyocyte subtypes selected from the group of atrial, ventricular and pacemaker cells.

An enriched cell population may be a cell culture that contains more than 50% of the desired differentiated cells, preferably more than 60%, 70%, 80%, 90%, or 95% of differentiated cells.

In embodiments, the starting cell population may contain wild-type pluripotent stem cells or pluripotent stem cells of a genetically modified cell lineage. Genetically modified cells generally comprise specific resistances, usually antibiotic resistances such as puromycin, bleomycin, hygromycin or neomycin resistance, or selection markers, usually fluorescence markers or membrane-bound cell surface markers. An elimination or enrichment may be effected in partially or pre-purified populations, such as puromycin-purified populations of genetically modified cells that express puromycin resistance marker in a cell-type-specific manner, but advantageously also can be used in wild-type cell populations without the need for genetic lineage selection approaches or other purification techniques. In other words, an enrichment using the compounds may be performed in combination with a puromycin-selection in respective modified cell lines, for example as an additional step, or may be performed in wild-type cells without further selection features. Enabling the use of wild-type cells provides a huge advantage.

The small molecule-based elimination of pluripotent stem cells using the compounds of formula (1) has significant advantages over a genetic selection as an entire cardiomyocyte population independent of subtype can be provided and results in higher cardiomyocyte yields than a transgenic approach such as using puromycin. A higher degree of heterogeneity of differentiated cardiomyocyte populations can be provided which may represent an advantage for specific in vitro or in vivo applications. In embodiments, the method thus is a non-transgenic method and/or a resistance or a selection marker-free method. Advantageously, the method provides an enrichment of cardiomyocytes without the need for genetic lineage selection approaches. Particularly, a standard antibiotic based such as a puromycin-based selection and enrichment may be avoided.

The compounds may be included in the manufacturing and scale-up production of a cell therapy product, potentially eliminating undifferentiated cells, for example pluripotent stem cells, thereby providing an improved measure of safety for pharmaceutical or cell therapeutic compositions.

Also provided are compositions that include pluripotent stem cells and differentiating or differentiated derivatives and a compound according to the general formula (1). The composition may be a differentiation culture in which the inhibition or removal of pluripotent stem cells is required, such as where the cells will be used for implantation therapy or for in vitro purposes, such as drug development or toxicity testing. A further aspect thus relates to a composition comprising pluripotent stem cells and differentiating cells or differentiated cells derived from the pluripotent stem cells, and a compound according to the general formula (1) and/or racemates, enantiomers, stereoisomers, solvates, hydrates or salts thereof:

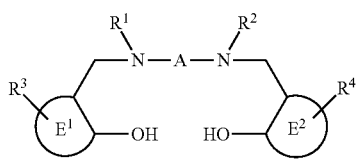

wherein:
$R^1$, $R^2$ the same or independent from each other are hydrogen or represent a double bond from the nitrogen atom to the adjacent non-cyclic carbon atom;
$R^3$, $R^4$ are the same or independently from each other selected from the group comprising hydrogen, linear or branched $C_1$-$C_8$-alkyl, $C_2$-$C_8$-alkenyl, $C_3$-$C_8$-cycloalkyl, $C_6$-$C_{10}$-aryl, $C_1$-$C_8$-alkoxy and halogen;

$E^1$, $E^2$ are the same or independent from each other a 5- or 6-membered aromatic or heteroaromatic ring selected from the group comprising thiophenyl, pyrrolyl, pyridyl and phenyl;
A is selected from the group of structural elements of formulas (2) and (3):

wherein:
B is selected from the group comprising $C_3$-$C_8$-cycloalkyl, $C_3$-$C_8$-heterocycloalkyl, $C_6$-$C_{10}$-aryl and $C_5$-$C_{10}$-heteroaryl;
Z is the same or independently from each other selected from the group comprising —$CH_2$—, —CHR'—, O, S, NH, NR';
R' is the same or independently from each other selected from the group comprising hydrogen, $C_1$-$C_8$-alkyl, $C_2$-$C_8$-alkenyl, $C_3$-$C_8$-cycloalkyl and $C_6$-$C_{10}$-aryl;
n, m are the same or independent from each other 0, 1 or 2;
p is 1, 2, 3, 4 or 5.

The bridging element A may comprise 2, 3 or more carbon atoms or hetero atoms, but other from that A may vary in its structure. A may be a structural element of formula (2) being or comprising a cyclic structure, or A may be a linear structural element of formula (3). Referring to the structural element of formula (3) —CHR'—$(Z)_p$— the element Z preferably may be a group —CHR'— and/or p preferably may be 1 or 2. R' preferably may be selected from hydrogen, $C_1$-$C_3$-alkyl or phenyl. In embodiments, A may be selected from —$CH_2$—$CH_2$—, —$(CH_2)_3$— or —$(CHphenyl)_2$-, preferably —$CH_2$—$CH_2$—. Preferably, A is a structural element of formula (2) —$(Z)_n$—B—$(Z)_m$—. Referring to the structural element of formula (2) Z preferably may be a group —$CH_2$— and/or m and n preferably may be 0 or 1. Preferably, m and n are the same 0 or 1. In embodiments, A is a structural element of formula (2) wherein n and m are 0. In embodiments of A being a structural element of formula (2) wherein n and m are 0, A is identical to B. In preferred embodiments, A or B is a 3- to 10-membered carbocyclic, heterocyclic, aromatic or heteroaromatic ring moiety selected from the group comprising $C_3$-$C_8$-cycloalkyl, $C_3$-$C_8$-heterocycloalkyl, $C_6$-$C_{10}$-aryl and $C_5$-$C_{10}$-heteroaryl. The ring moieties include bicyclic groups in which a 5- or 6-membered ring is fused to a further ring, such as a benzene ring. A ring moiety advantageously provides for the stability of the bridging element A. The element A or B may be selected from the group comprising benzene, furan, tetrahydrofuran, thiophene, tetrahydropyran, pyrrole, pyrrolidine, imidazole, piperidine, piperazine, pyridine, pyrimidine or morpholine. Preferably, A or B may be a 5- or 6-membered carbocyclic, heterocyclic, aromatic or heteroaromatic ring. In preferred embodiments, A is a 5- or 6-membered carbocyclic ring selected from the group comprising cyclopentyl and/or cyclohexyl. In further embodiments, A or B may be a 6-membered heteroaromatic ring selected from the group consisting of pyridyl, pyridazyl, pyrimidyl and/or pyrazyl, or a 5-membered heteroaromatic ring selected from the group consisting of thiazolyl, oxazolyl, imidazolyl, pyrazolyl, thiophenyl, furyl and/or pyrrolyl. The amine or imine groups, particularly diamine groups preferably are bound in a 1,2-, 1,3- or 1,4-fashion to a ring element A or B, particularly to a 5- or 6-membered carbocyclic, heterocyclic, aromatic or heteroaromatic ring. Preferably, the amine or imine groups, particularly diamine groups are bound in a 1,2-fashion. Most preferably, the element A is cyclohexyl and the diamine groups are bound in a 1,2-fashion. The elements $E^1$ and $E^2$ preferably are the same and selected from pyridyl or phenyl, particularly $E^1$ and $E^2$ are phenyl rings.

In embodiments, the compound is a compound according to general formula (4). In embodiments of the compound of formula (1) and the compound of formula (4), at least one of $R^1$ and $R^2$ are hydrogen. In embodiments, $R^1$ and $R^2$ both are hydrogen. In embodiments, $R^3$ and $R^4$ are the same or independently from each other selected from the group comprising hydrogen, linear or branched $C_1$-$C_5$-alkyl, and phenyl. Preferred linear or branched $C_1$-$C_5$-alkyl groups are selected from methyl, ethyl and t-butyl. In preferred embodiments, $R^3$ and $R^4$ are the same, and selected from the group of hydrogen and phenyl. In preferred embodiments, $R^1$ and $R^2$ are the same or independent from each other hydrogen or represent a double bond from the nitrogen atom to the adjacent non-cyclic carbon atom, and $R^3$ and $R^4$ are the same or independently from each other selected from the group comprising hydrogen, linear or branched $C_1$-$C_5$-alkyl, and phenyl. Preferably, at least one or both of $R^1$ and $R^2$ are hydrogen, and $R^3$ and $R^4$ are the same and selected from the group of hydrogen and phenyl. In preferred embodiments, the compound is selected from the group of compounds according to formulas (5), (6) and (7) and/or racemates, enantiomers, stereoisomers, solvates, hydrates or salts thereof. In preferred embodiments, the compound is selected from the group of compounds according to formulas (SM1), (SM2), (SM4), (SM5), (SM6) and (SM8). In preferred embodiments, the compound is selected from the group of compounds according to formulas (SM6), (SM2) and (SM8). Most preferred is the compound (SM6). In embodiments, the composition may comprise the compound according to general formula (1) or a compound of formula formulas (4) to (7), (SM6), (SM2) and (SM8) in a range from ≥0.01 μM to ≤100 μM, preferably in a range from ≥0.05 μM to ≤10 μM, more preferably in a range from ≥0.05 μM to ≤2 μM.

For the description of the pluripotent stem cells and the differentiating cells or differentiated cells derived from the pluripotent stem cells, reference is made to the description above.

A further aspect relates to a composition comprising a differentiated cell population obtained by a method according to the invention. The composition may be pharmaceutical composition or a diagnostic composition. A pharmaceutical composition may be usable in cell therapeutic therapies, while a diagnostic composition may be usable in in vitro diagnostic purposes or drug screening or toxicity testing. In embodiments, the composition comprising a differentiated cell population obtained by a method according to the invention is for use in a cell transplantation therapy.

The differentiated cell population may comprise cardiomyocytes, or enriched cardiomyocyte subtypes selected from the group of atrial, ventricular, and pacemaker cells. The pharmaceutical or cell therapeutic composition further may comprise further agents usable in cell-based regenerative therapies and therapeutic treatments based on the injection of living cells in clinical use. Such agents may be selected from other cell types, such as adult stem cells or their derivatives, or cells derived from pluripotent stem cells, bioactive agents such as growth factors, small molecules, non-coding RNAs, exosomes, and others, biomaterials and synthetic nanomaterials, such as complex nanocarriers.

A further aspect relates to a compound according to the following general formula (1) and/or racemates, enantiomers, stereoisomers, solvates, hydrates or salts thereof:

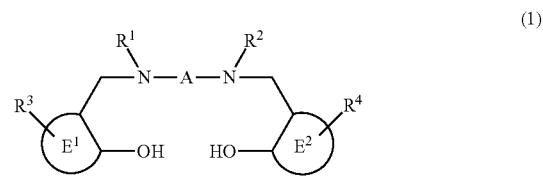

(1)

wherein:
$R^1$, $R^2$ the same or independent from each other are hydrogen or represent a double bond from the nitrogen atom to the adjacent non-cyclic carbon atom;
$R^3$, $R^4$ are the same or independently from each other selected from the group comprising hydrogen, linear or branched $C_1$-$C_8$-alkyl, $C_2$-$C_8$-alkenyl, $C_3$-$C_8$-cycloalkyl, $C_6$-$C_{10}$-aryl, $C_1$-$C_8$-alkoxy and halogen;
$E^1$, $E^2$ are the same or independent from each other a 5- or 6-membered aromatic or heteroaromatic ring selected from the group comprising thiophenyl, pyrrolyl, pyridyl and phenyl;
A is selected from the group of structural elements of formulas (2) and (3):

  (2)

  (3)

wherein:
B is selected from the group comprising $C_3$-$C_8$-cycloalkyl, $C_3$-$C_8$-heterocycloalkyl, $C_6$-$C_{10}$-aryl and $C_5$-$C_{10}$-heteroaryl;
Z is the same or independently from each other selected from the group comprising —$CH_2$—, —CHR'—, O, S, NH, NR';
R' is the same or independently from each other selected from the group comprising hydrogen, $C_1$-$C_8$-alkyl, $C_2$-$C_8$-alkenyl, $C_3$-$C_8$-cycloalkyl and $C_6$-$C_{10}$-aryl;
n, m are the same or independent from each other 0, 1 or 2;
p is 1, 2, 3, 4 or 5,
for use in the reduction of the number or percentage of pluripotent stem cells or the enrichment of differentiated cells in a cell population comprising pluripotent stem cells and differentiating cells or differentiated cells derived from the pluripotent stem cells.

This aspect particularly relates to a use of a compound according to the general formula (1), or a compound of formulas (4) to (7), particularly of formulas (SM1), (SM2), (SM4), (SM5), (SM6) and (SM8) in the reduction of the number or percentage of pluripotent stem cells or the enrichment of differentiated cells in a cell population comprising pluripotent stem cells and differentiating cells or differentiated cells derived from the pluripotent stem cells.

For the description of the pluripotent stem cells and the differentiating cells or differentiated cells derived from the pluripotent stem cells, the compounds and methods reference is made to the description above.

The invention further relates to a method of reducing the number or percentage of pluripotent stem cells or of enriching differentiating or differentiated cells in a cell population comprising pluripotent stem cells and differentiating cells or differentiated cells derived from the pluripotent stem cells, the method comprising the step of contacting the cell population with a compound selected from the group of compounds according to formulas (SM20), (SM21), (SM22) and (SM23) as given as follows and/or solvates, hydrates or salts thereof:

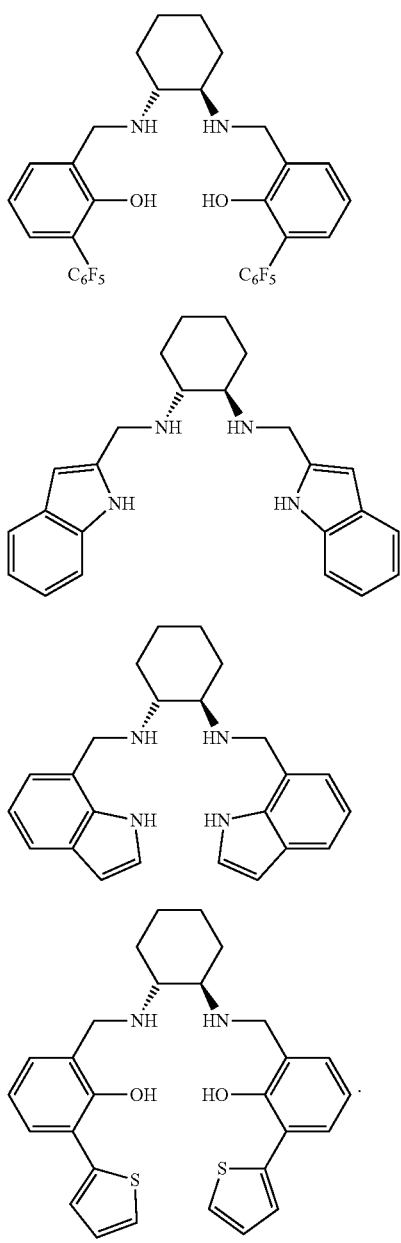

Also the compounds of formulas (SM20), (SM21), (SM22) and (SM23) are usable for the elimination of pluripotent stem cells. The compounds of formulas (SM20), (SM21), (SM22) and (SM23) exhibited high cytotoxicity to pluripotent stem cells. The method thus preferably is a method of eliminating pluripotent stem cells (PSCs), particularly induced pluripotent stem cells (iPSCs) or embryonic stem cells (ESCs) but also other pluripotent stem cell types such as parthenogenetic pluripotent stem cells (pgPSCs) and pluripotent stem cells derived by somatic cell nuclear transfer (SCNT) technology (scntPSCs), in a cell population comprising pluripotent stem cells and differentiating or differentiated cells derived from the pluripotent stem cells.

The compounds according to formulas (SM20), (SM21), (SM22) and/or (SM23) may be usable in the form of solvates, hydrates, and salts such as pharmaceutically acceptable salts. In embodiments, the step of contacting the cell population with a compound comprises incubating the cell population in a cell culture medium containing a compound according to formulas (SM20), (SM21), (SM22) and/or (SM23) in a range from ≥0.01 µM to ≤100 µM, preferably in a range from ≥0.05 µM to ≤10 µM, more preferably in a range from ≥0.05 µM to ≤2 µM.

In embodiments, the pluripotent stem cells (PSCs) are induced pluripotent stem cells (iPSCs) or embryonic stem cells (ESCs) or parthenogenetic pluripotent stem cells (pgPSCs) or pluripotent stem cells derived by somatic cell nuclear transfer (SCNT) technology (scntPSCs). In preferred embodiments, the pluripotent stem cells are human induced pluripotent stem cells (hiPSCs) or humen embryonic stem cells (hESCs). In embodiments the cells are mammalian cells, particularly primate cells, such as human cells. In preferred embodiments, the pluripotent stem cells are human cells. Differentiating or differentiated cells are typically derived from pluripotent stem cells of various types such as ESCs, iPSC, pgPSCs, and may include such cells as cardiomyocytes, insulin-producing β-cells, smooth muscle cells, liver cells, as well as different types of neuronal cells, blood cells, retinal cells, and other cell types. In preferred embodiments, the differentiating or differentiated cells are cardiomyocytes. In embodiments, the cardiomyocyte subtypes are selected from the group of atrial (AM), ventricular (VM), and pacemaker (PM) cells. In embodiments, the method is a method for enriching cardiomyocyte subtypes selected from the group of atrial, ventricular and pacemaker cells. In embodiments, the method thus is a non-transgenic method and/or a resistance- or a selection marker-free method.

Also provided is a composition comprising pluripotent stem cells and differentiating cells or differentiated cells derived from the pluripotent stem cells, and a compound selected from the group of compounds according to formula (SM20), (SM21), (SM22) and (SM23) and/or solvates, hydrates or salts thereof. In embodiments, the composition may comprise a compound according to formulas (SM20), (SM21), (SM22) and/or (SM23) in a range from ≥0.01 µM to ≤100 µM, preferably in a range from ≥0.05 µM to ≤10 µM, more preferably in a range from ≥0.05 µM to ≤2 µM.

A further aspect relates to a composition comprising a differentiated cell population obtained by a method using a compound selected from the group of compounds according to formulas (SM20), (SM21), (SM22) and (SM23), particularly for use in a cell transplantation therapy.

A further aspect relates to a use a compound selected from the group of compounds according to formula (SM20), (SM21), (SM22) and (SM23) and/or solvates, hydrates or salts thereof in the reduction of the number or percentage of pluripotent stem cells or the enrichment of differentiated cells in a cell population comprising pluripotent stem cells and differentiating cells or differentiated cells derived from the pluripotent stem cells.

For a further description of the pluripotent stem cells and the differentiating cells or differentiated cells derived from the pluripotent stem cells, the compositions, the use and the method, reference is made to the description above.

A further aspect relates to a compound selected from the group of compounds according to formulas (SM20), (SM21), (SM22) and (SM23) as given as follows and/or solvates, hydrates or salts thereof:

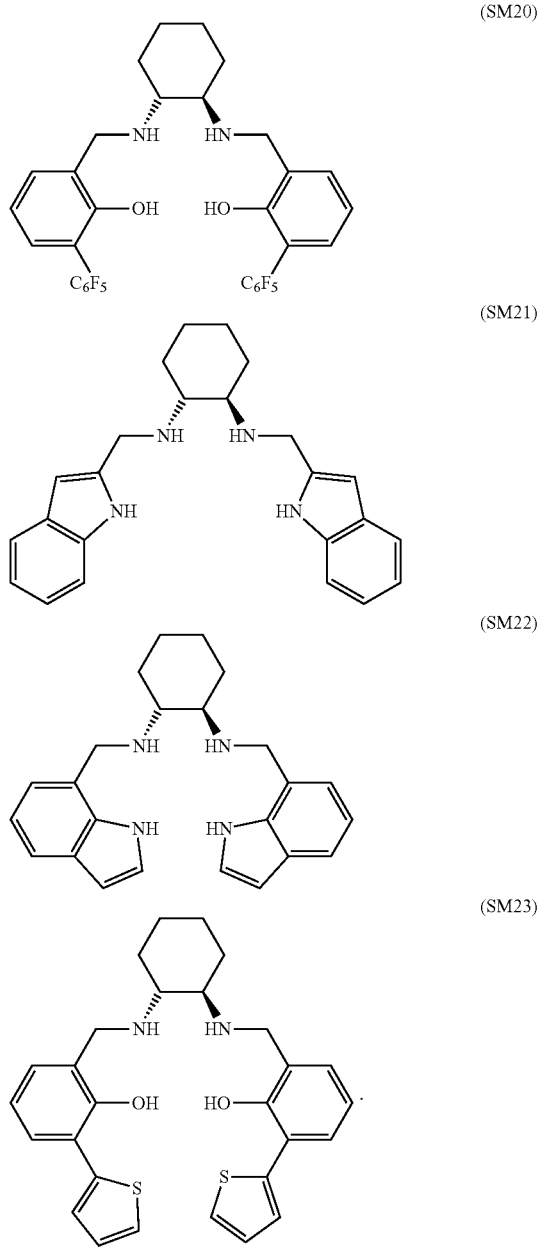

Unless otherwise defined, the technical and scientific terms used herein have the same meaning as commonly understood by one of ordinary skill in the art to which this invention belongs.

The examples that follow serve to illustrate the invention in more detail but do not constitute a limitation thereof.

The figures show:

FIG. 1 The relative viability of murine iPSCs (miPSCs) after 48 h of treatment with 0.1 µM, 1 µM, 10 µM and 25 µM of the compounds according to formulas SM1 to SM10 (mean±SD; n=4). Cells treated with DMSO served as negative control and cells treated with puromycin (8 µg/ml) served as positive control for cytotoxicity.

Figure 2:
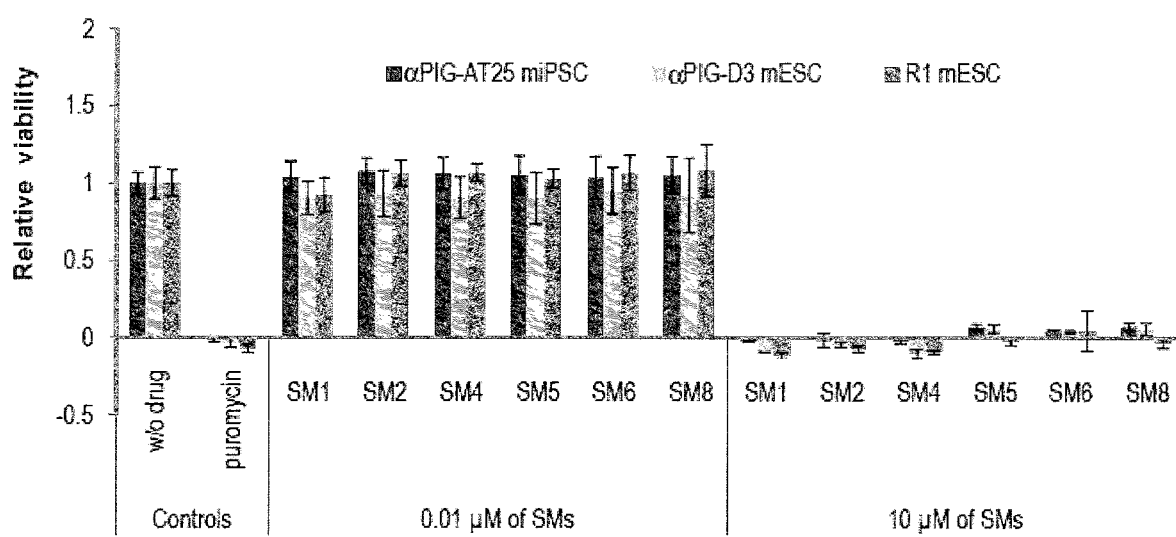

FIG. 2 The relative viability of three different lines of murine PSCs (one iPSC line and two ESC lines) after 48 h of treatment with nontoxic 0.01 µM and PSC-eliminating 10 µM of compounds (mean±SD; n=4, p>0.05).

Figure 3:
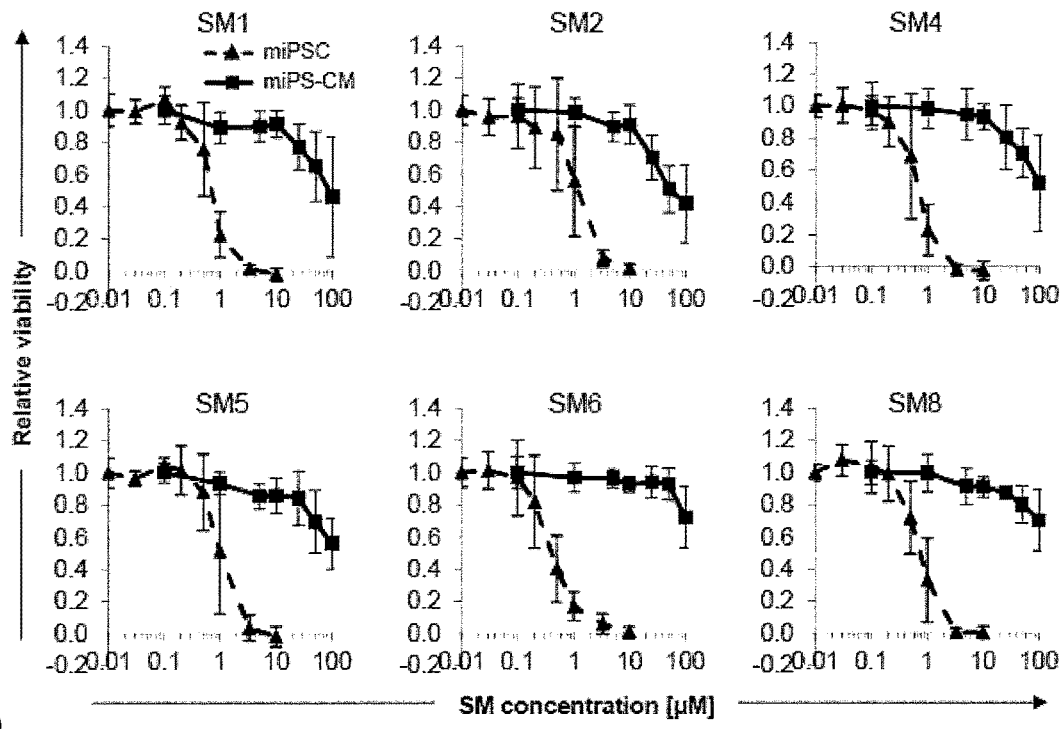
Figure 3:
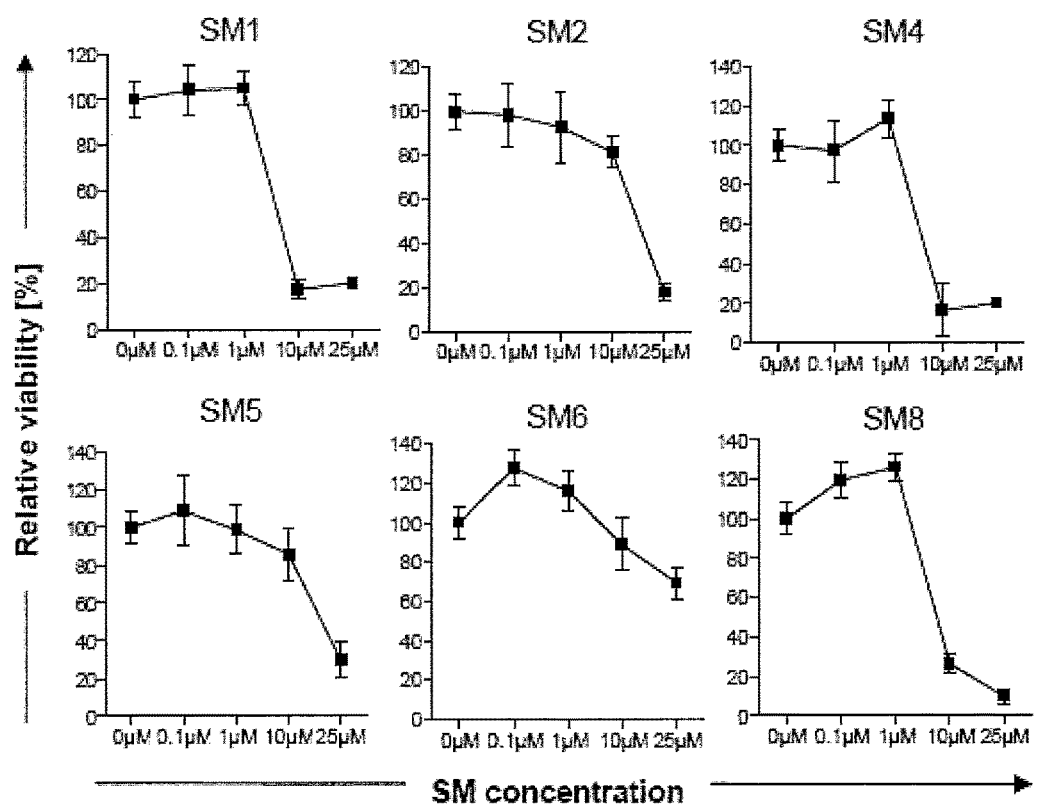

FIG. 3 FIG. 3a) shows the relative viability of αPIG-AT25 miPSCs and the miPSC-derived cardiomyocytes (miPSC-CM) after 48 h of treatment with compounds (mean±SD; n=4-20), and FIG. 3b) shows the relative viability of αPIG-AT25 miPSC-derived cardiomyocytes after 72 h of treatment with compounds (mean±SD; n=4).

Figure 4:
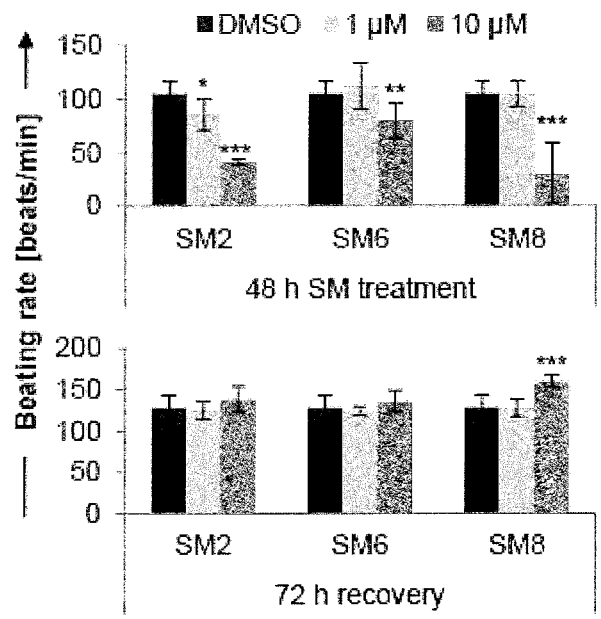

FIG. 4 The cardiomyocyte contraction rates after compound treatment for 48 h and after 72 h of subsequent recovery without the substance (mean±SD; n=8).

Figure 5:
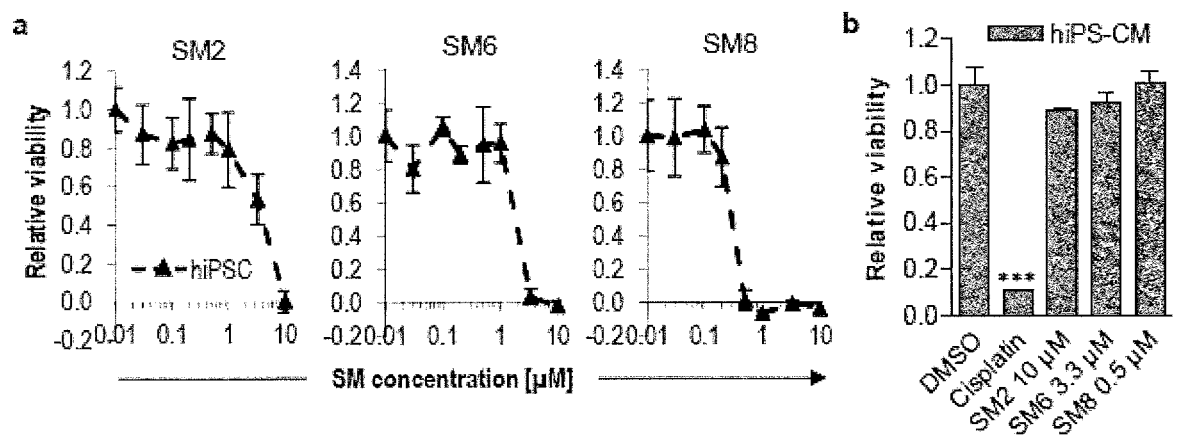

FIG. 5 FIG. 5a) shows the relative viability of human iPSCs (cell line NP0014-C6) after 48 hr treatment with different concentrations of compounds (mean±SD; n=4) and FIG. 5b) shows the relative viability of human iPSCs-derived CMs after 48 hr treatment with indicated concentrations of compounds (mean±SD; n=3).

Figure 6:
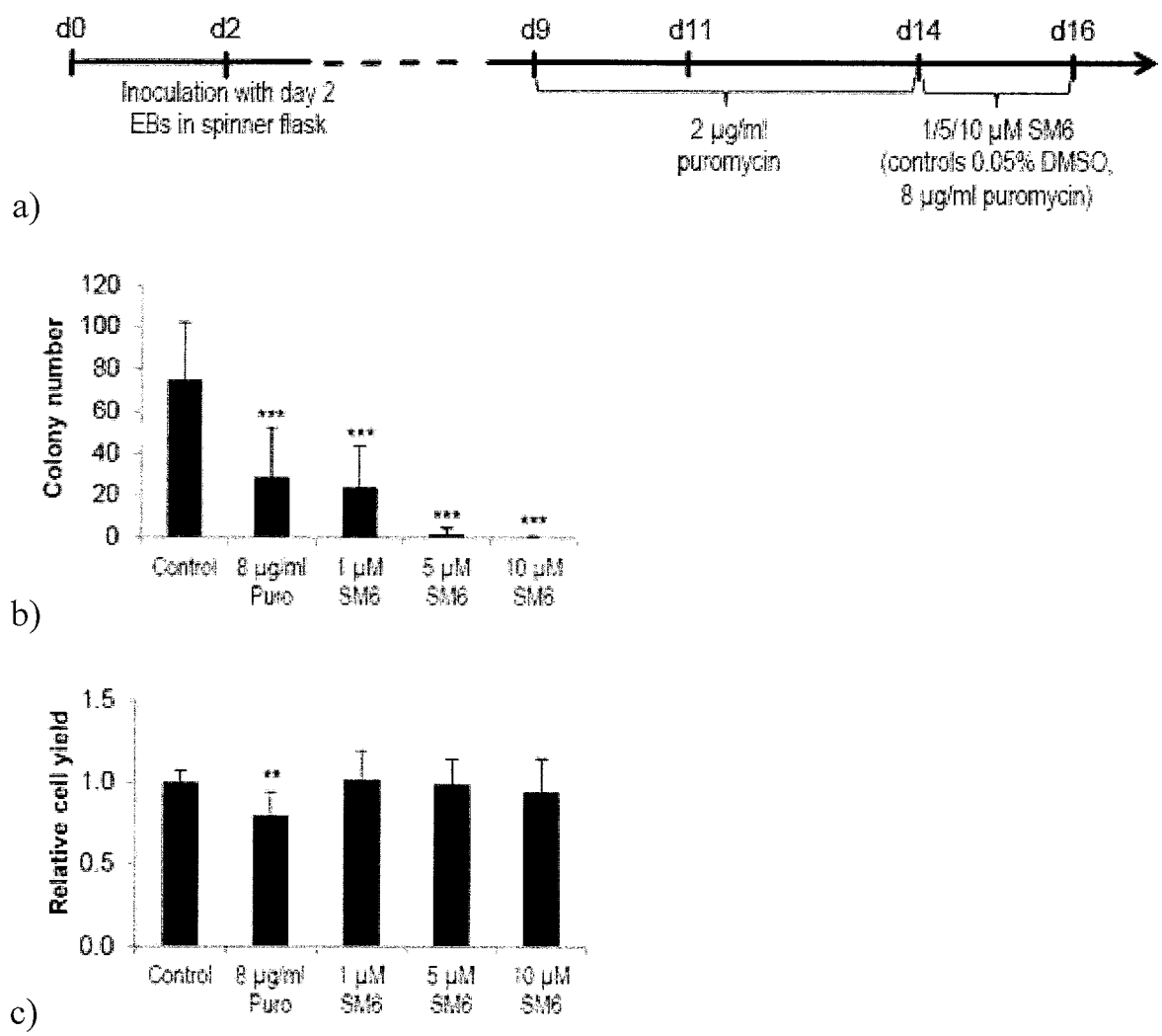

FIG. 6 FIG. 6a) shows the time course of miPSC cardiogenic differentiation and treatment with compound SM6. FIG. 6b) shows the quantification of iPSC colonies grown after plating of 2×10⁵ cells derived from dissociated day 16 cardiac clusters after treatment with indicated substances (mean±SD; n=19). FIG. 6c) shows the relative cardiomyocyte yield in SM6-treated cardiac clusters from day 16 of differentiation compared to DMSO- and puromycin-treated controls (mean±SD; n=9).

Figure 7:
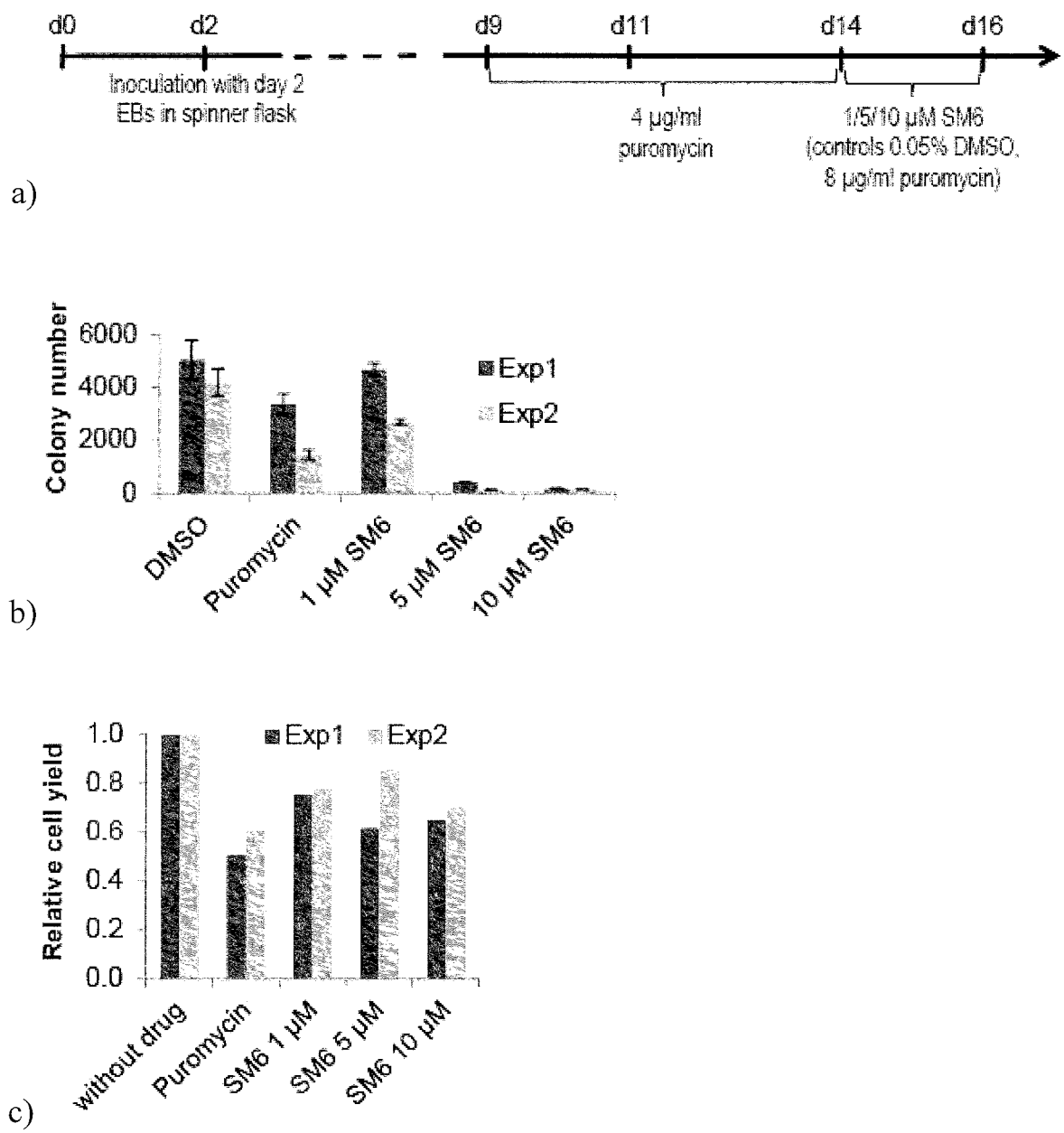

FIG. 7 FIG. 7a) shows the time course of murine ESC (mESC) cardiogenic differentiation and treatment with compound SM6. FIG. 7b) shows the quantification of ESC colonies grown after plating of 2×10⁵ cells derived from dissociated day 16 cardiac clusters after treatment with indicated substances (mean±SD; n=3). FIG. 7c) shows the relative cell yield in SM6-treated cardiac clusters from day 16 of differentiation compared to DMSO- and puromycin-treated controls. Results from two independent experiments are shown.

Figure 8:
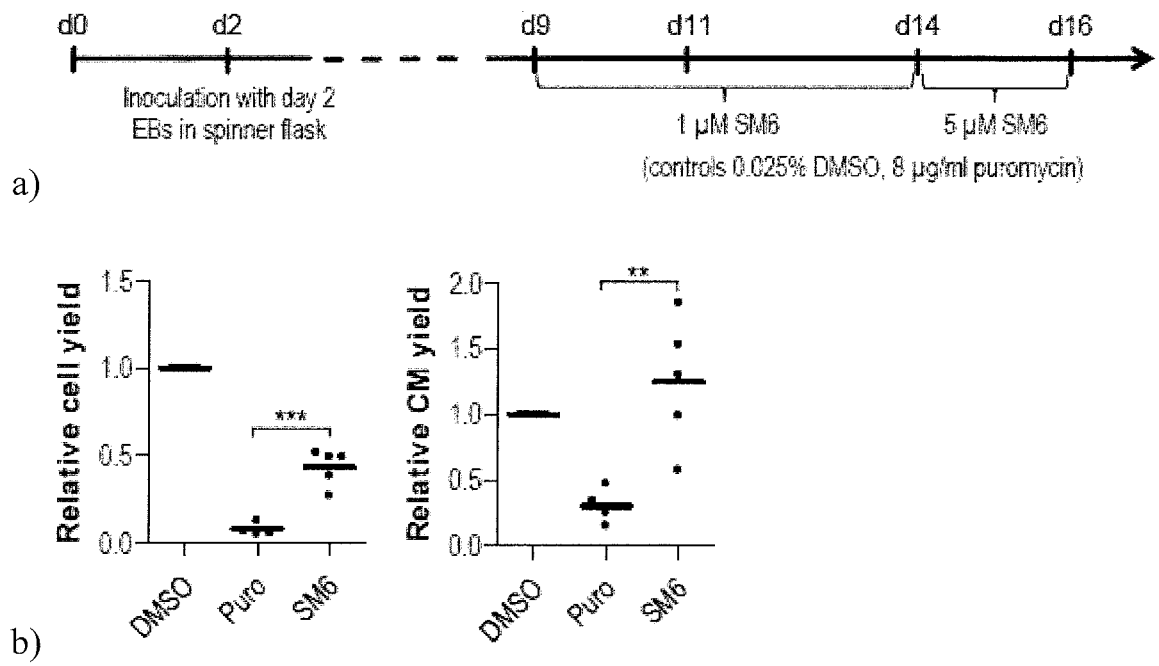

FIG. 8 FIG. 8a) shows the time course of mESC cardiogenic differentiation and treatment with compound SM6 without previous puromycin treatment. FIG. 8b) shows the relative cell yield and the relative cardiomyocyte yield in SM6-treated cardiac clusters from day 16 of differentiation compared to DMSO-treated controls and puromycin-treated cells.

Figure 9:
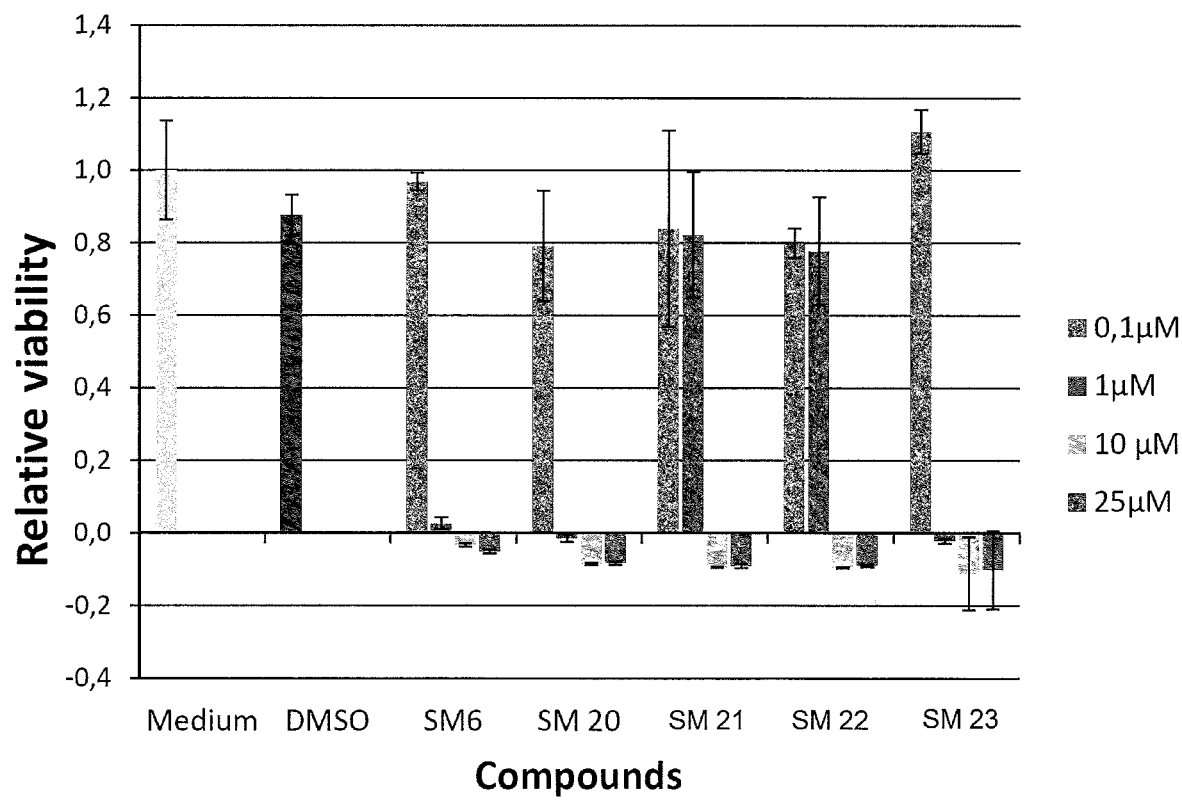

FIG. 9 The relative viability of the miPSCs after 48 h of treatment with 0.1 µM, 1 µM, 10 µM and 25 µM of the compounds SM20, SM21, SM22 and SM23.

Figure 10:
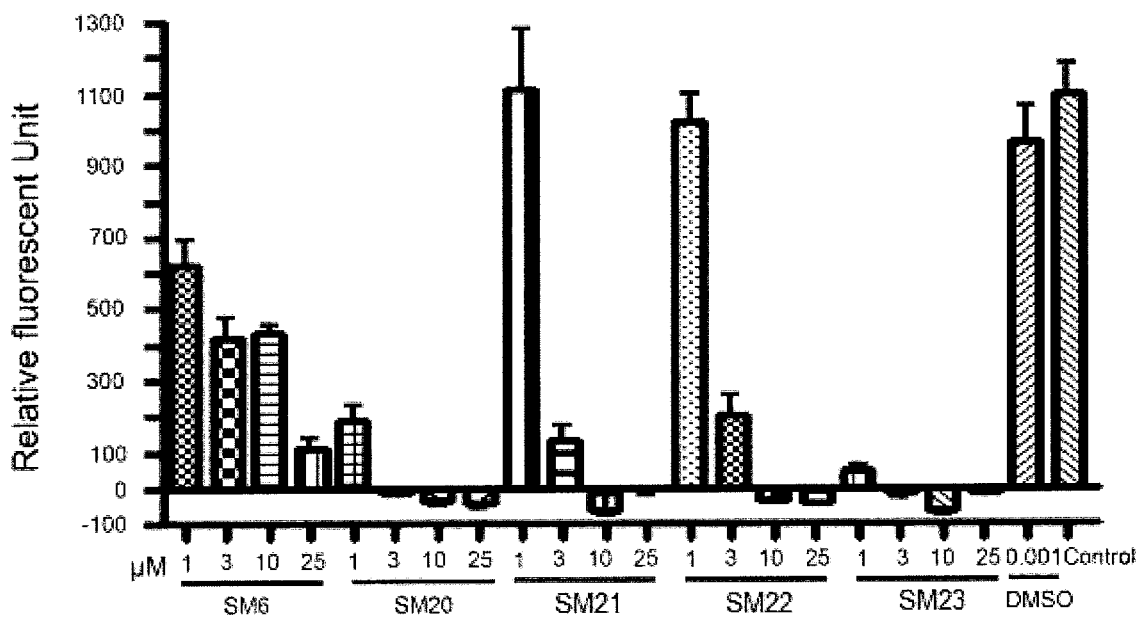
Figure 10:
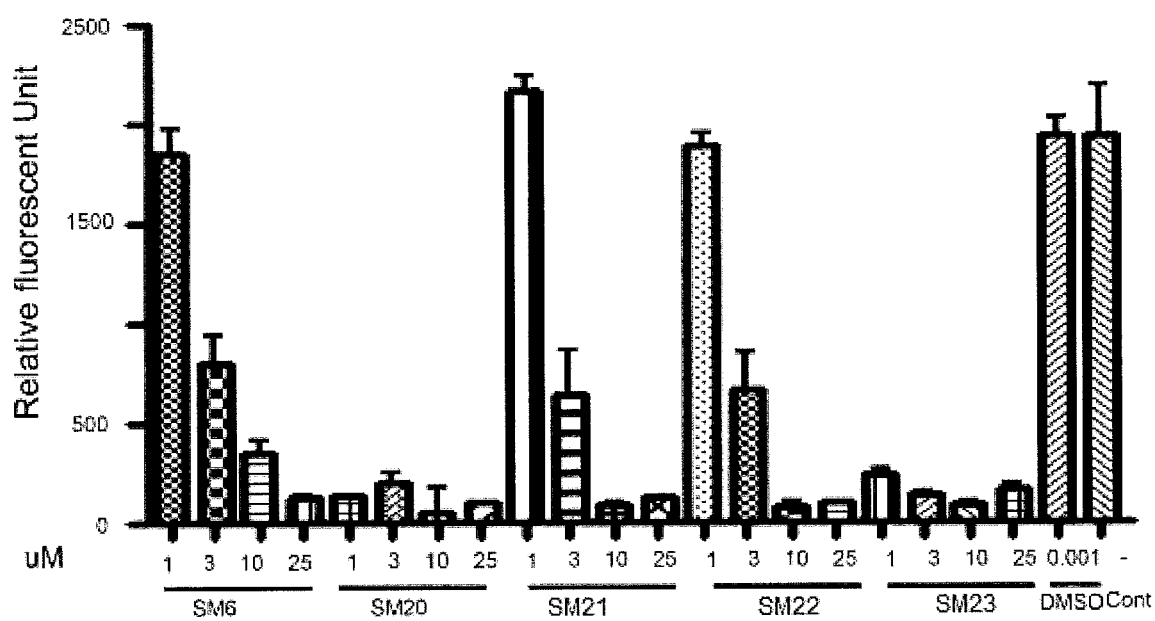
Figure 10:
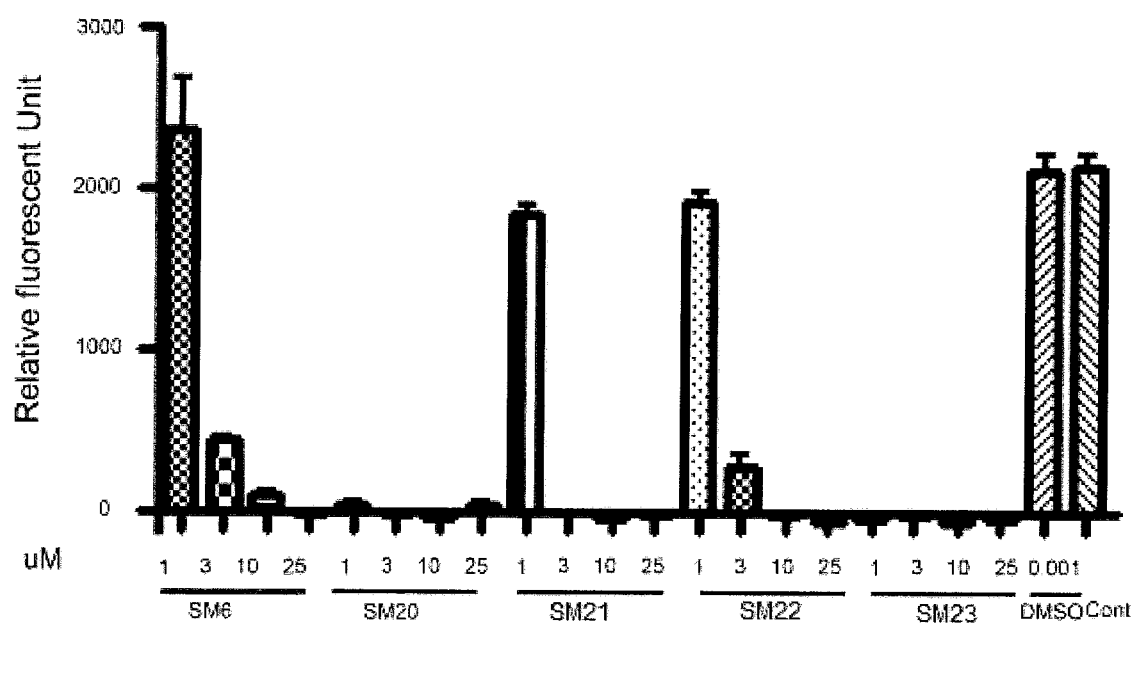

FIG. 10 The relative viability of human NPCs after 24 h, 48 h or 72 h of treatment with 1 µM, 3 µM, 10 µM or 25 µM of the compounds SM20, SM21, SM22 and SM23 in FIGS. 10a), 10b) and 10c), respectively.

METHODS

Cell Culture:

The transgenic murine induced pluripotent stem cell (miPSC) line αPIG-AT25 was generated from the miPSC line TiB7.4 as described in Fatima A et al., Stem Cell Res. 2016 Sep.; 17(2):266-272. The murine embryonic stem cell (ESC) line αPIG44-D3 was equally derived from D3 ESC line. Both transgenic mPSC lines express the IRES-linked genes encoding puromycin N-acetyl-aminotransferase (PAC) and enhanced green fluorescent protein (eGFP) which are under the control of cardiac alpha myosin heavy chain (α-MHC) promoter. They were cultured on mitomycin-inactivated mouse embryonic fibroblasts (MEF) in maintenance medium composed of Dulbecco's minimal essential medium (DMEM) with GlutaMAX (Life Technologies, Carlsbad, USA) supplemented with 15% fetal bovine serum (FBS, Sigma-Aldrich, St. Louis, USA), 1× non-essential amino acids (NEEA, Life Technologies), 50 µM β-mercaptoethanol (β-ME, Life Technologies) and 1000 U/ml of murine leukemia inhibitory factor (mLIF, ORF Genetics, Kopavogur, Iceland). Cell passaging was performed every 2-3 days by dissociating the cells with 0.05% trypsin-EDTA (Life Technologies) and seeding 1-2×10$^4$ cells/cm$^2$. The wild type mESC line R1 was cultured on cell culture plates coated with 0.1% gelatin (Sigma-Aldrich) and maintained like the transgenic mPSCs.

Human iPSC line NP0014-C6 was generated from skin fibroblasts of a patient with catecholaminergic polymorphic ventricular tachycardia (CPVT, hPSCreg name: UKKi007-A). This iPSC line was obtained from human dermal fibroblasts after insertion-free reprogramming with episomal plasmid vectors developed by Shinya Yamanaka laboratory as described in Fatima A et al., Cell Physiol Biochem. 2011; 28(4):579-92. Human iPSCs were maintained in E8 medium (Life Technologies) on cell culture plates pre-coated with 5 µg/ml vitronectin (Life Technologies). At 70-80% of confluence, hiPSCs were passaged as aggregates every 4-5 days by gentle dissociation with 0.48 mM Versene solution (Life Technologies).

Cardiac Differentiation:

The differentiation of transgenic mPSCs was initiated in mass cultures as briefly described below. One million cells were transferred per non-adhering 10 cm dish with 14 ml differentiation medium composed of Iscove's Modified Dulbecco's Medium (IMDM) with GlutaMAX (Life Technologies) supplemented with 20% FBS, 1×NEAA and 100 µM β-ME. Embryoid bodies (EBs) from day 2 of differentiation were transferred in a 250 ml spinner flask (CELLSPIN 250, Integra Biosciences, Fernwald, Germany) with a density of 3×10$^4$ EBs per 200 ml of differentiation medium. On the first 2 days of differentiation medium was supplemented with 50 µg/ml L-ascorbic acid phosphate (AA, Wako pure chemicals industry, Japan) in order to promote the development of cardiac cells. For the selection of GFP-expressing CMs, 50 ml of the medium was exchanged with fresh differentiation medium and 8 µg/ml puromycin (Life Technologies) were supplemented on day 9 of differentiation. Two days later, the cardiac clusters were transferred on non-adhering 10 cm dishes with fresh differentiation medium containing 8 µg/ml puromycin. In the further course of differentiation medium was exchanged every 2-3 days. If not otherwise specified, the purification of GFP-positive CMs with puromycin was continued until day 16 of differentiation. For single cell analyses and transfer of PSC-derived CMs on cell culture plates, cardiac clusters were dissociated with 0.25% trypsin-EDTA (Life Technologies) supplemented with 50 U/ml DNase I (AppliChem, Darmstadt, Germany) for 20-30 min at 37° C. The mPSC-derived CMs were filtered through a polyamide membrane with 60 µM pore size (Sefar, Heiden, Switzerland). Cell numbers were determined with a Neubauer hemocytometer and cells were stored on ice until further use.

The transgenic puromycin-selected Cor.4U hiPSC-derived CMs (hiPSC-CM) were provided by Axiogenesis (Cologne, Germany). Thawing and seeding of the cryopreserved cells were performed following the manufactures recommendations.

Dose Response Assays:

Serial dilutions of DMSO stock solutions of PluriSIn #1 (Sigma-Aldrich, catalog number SML0682) or one of small molecules SM1-SM10, were prepared from 20 mM stock solutions with cell culture medium. Murine PSCs were dissociated with 0.05% trypsin-EDTA, seeded on 0.1% gelatin-coated 96-well plates with a density of 5000 cells/well and cultured in maintenance medium supplemented with 1000 U/ml of mLIF. After 1 day, cells were incubated with 40 µM PluriSIn #1 and derivatives for 72 h or with 0.01-25 µM SMs for 48 h, respectively. For treatment of corresponding PSC-derived CMs with SMs, puromycin-selected miPSC-CMs from day 14 of differentiation were dissociated with 0.25% trypsin-EDTA as described above and plated on 96-well plates (5×10$^4$ cells/well) which were pre-coated with 5 µg/ml fibronectin (PromoCell, Heidelberg, Germany). After culturing miPSC-CMs with 8 µg/ml puromycin for 2 more days, they were incubated in differentiation medium supplemented with 0.1-100 µM of SMs for 48-72 h. Following small molecule treatment, cell viability was determined with PrestoBlue cell viability reagent (Life Technologies). To this end, cells were washed with PBS (with calcium and magnesium, Life Technologies) and incubated with PrestoBlue reagent diluted in cell culture medium for 40 min at 37° C.

Fluorescence intensities correlating with the number of viable cells in the wells were measured in black flat-bottom 96-well plates (Greiner Bio-One, Kremsmünster, Austria) with a GeniosPro microplate reader (Tecan, Männedorf, Schweiz).

IC$_{50}$ values were determined by regression analysis of dose-response curves upon logarithmic transformation. Microscopic images of PSCs were taken with a Zeiss Axiovert 100 inverted microscope and GFP images of CMs were captured with a Zeiss Axiovert 200M fluorescence microscope (both Carl Zeiss, Oberkochen, Germany) and analyzed with Zeiss Axiovision 4.5 software (Carl Zeiss).

Cardiomyocyte (CM) Contraction Rate:

The effect of compound treatment on CM beating frequency was determined by video imaging of iPSC-CM monolayers after exposure to SMs. On day 14 of differentiation puromycin-selected miPSC-CMs were plated on a fibronectin-coated multi-well cell culture plate (10$^5$ cells/cm$^2$). After maintaining the CMs in differentiation medium with 8 µg/ml puromycin for 2 days, medium was refreshed and supplemented with 1 and 10 µM of SMs for 48 h. Following SM treatment, cells were washed twice with PBS (with calcium and magnesium) and cultured for 72 h in fresh differentiation medium. Videos of CM monolayers were recorded right after 48 h of SM treatment and after 72 h of recovery using an Axiovert100 inverted microscope and a DFW-X710 digital camera (Sony, Tokyo, Japan). The number of beats per each video sequence was quantified and the contraction rate was calculated in beats per minute.

Immunocytochemistry (ICC):

Cardiomyocyte (CM) sarcomeric integrity and apoptosis inducing effects after SM treatment were analyzed by staining of α-actinin and cleaved caspase 3. Purified day 14 miPSC-CMs were plated on fibronectin-coated multi-well cell culture plates (10$^5$ cells/cm$^2$) and treated with 8 µg/ml puromycin for two more days. Then the CM monolayer was treated with 1 and 10 µM of SMs for 48 h. Cisplatin was used as positive control in preparation of α-actinin (150 µg/ml cisplatin for 48 h) and cleaved caspase-3 (75 µg/ml cisplatin for 24 h) stainings. α-Actinin was immunocytochemically determined directly after 48 h of SM treatment. The cells were fixed with an ice-cold solution of methanol and acetone (1:1) for 10 min at −20° C. Then cells were permeabilized with 0.2% Triton-X 100 (Sigma-Aldrich) for 5 min, blocked with 5% bovine serum albumin (BSA, Applichem, Darmstadt, Germany) in PBS for 1 h at room temperature and incubated with an anti-α-actinin mouse antibody (1:800, A7811, Sigma-Aldrich) in 0.8% BSA in PBS overnight at 4° C. On the next day, cells were washed with PBS and incubated with an Alexa Fluor (AF) 555-conjugated goat anti-mouse secondary antibody (1:1000, A21127, Life Technologies) for 1 h at room temperature.

γ-H2AX and cleaved caspase-3 were stained after 48 h of SM treatment and after 72 h of recovery in culture medium without small molecules. Cells were fixed with 4% paraformaldehyde (PFA, Morphisto, Frankfurt am Main, Germany) for 15 min, permeabilized with 0.25% Triton-X 100 and 0.5 M $NH_4Cl$ (Roth, Karlsruhe, Germany) in PBS for 15 min and blocked with 5% BSA in PBS for 1 h at room temperature. An anti-γ-H2AX rabbit antibody (1:400, 9718, Cell Signaling) or an anti-cleaved-caspase-3 rabbit antibody (1:400, 9664, Cell Signaling) in 0.8% BSA in PBS was added overnight at 4° C., respectively. Cells were washed with PBS and incubated with an AF 555-conjugated goat anti-rabbit secondary antibody (1:1000, A21428, Life Technologies) for 1 h at room temperature.

The pluripotency of plated PSCs was confirmed by ICC stainings of transcription factors Oct4 and Nanog as well as cell surface antigens SSEA-4 and Tra-1-81. Cells were fixed in 4% PFA and permeabilized with 0.25% Triton-X 100 and 0.5 M $NH_4Cl$ diluted in PBS for 10 min at room temperature. After blocking with 5% BSA in PBS for 1 h at room temperature, cells were incubated with primary antibodies (anti-Oct4 mouse antibody (sc-5279,1:400), anti-Nanog rabbit antibody (sc-33759, 1:100), anti-SSEA-4 mouse antibody (sc-21704,1:200), anti-Tra-1-81 mouse antibody (sc-21706, 1:200), all from Santa Cruz) diluted in 0.8% BSA in PBS overnight at 4° C. On the next day cells were washed with PBS and incubated with respective AF conjugated secondary antibodies (goat anti-mouse IgG AF555 (A21425), goat anti-mouse IgG AF488 (A11001), goat anti-rabbit IgG AF555 (A21428), goat anti-mouse IgM AF555 (A21426), all from Life Technologies) diluted 1:1000 in 0.8% BSA in PBS for 1 h at room temperature.

Treatment of PSC-Derived Cell Aggregates and Colony Formation Assay:

Aiming at complete elimination of remaining PSCs in PSC-derived cell aggregates, murine cardiac clusters were pre-purified with 2-4 μg/ml puromycin from day 9 until day 14 of differentiation in order to prevent complete removal of PSCs and then treated with SM6 for 2 days to assess its potential for removal of contaminating PSCs in the absence of puromycin. After treatment, cardiac clusters were dissociated with 0.25% trypsin-EDTA supplemented with 50 U/ml of DNase I and the level of PSC contamination was determined using colony formation assay, flow cytometry for SSEA-1 and RT-PCR for Oct4. In colony formation assays $2 \times 10^5$ cells were plated on a 6 cm cell culture dish containing MEF and cultured in maintenance medium supplemented with 1000 U/ml of mLIF for 7-10 days. Developing PSC colonies on MEF plates were quantified and visualized with 1% crystal violet (Fluka Analytical, St. Louis, USA) diluted in methanol (Applichem).

Purifying the whole CM population including GFP-negative CMs in murine PSC-derived EBs was tested with SM6 as well. EBs from day 9 of differentiation were treated starting with 1 μM of SM6 for 5 days followed by treatment with 5 μM from day 14 until day 16 of differentiation. The percentage of CM population in EBs was monitored by flow cytometry and the amount of contaminating PSCs was quantified by colony formation assay as described above. Fluorescence images of PSC-derived cell aggregates were captured with a Zeiss Axiovert 200M fluorescence microscope and analyzed with Zeiss Axiovision 4.5 software.

Flow Cytometry:

Determination of CM purity in the cell population was performed by flow cytometric analysis. PSC-derived EBs or cardiac clusters were dissociated with 0.25% trypsin-EDTA. Dead cells were stained with LIVE/DEAD fixable dead cell stain kit (Life Technologies) prior to cell fixation using in 4% PFA for 15 min. Immunological staining of cardiac Troponin T (cTnT) was performed in order to detect the total CM population including GFP-negative CMs. Therefor, $5 \times 10^5$ cells were permeabilized in a 1% saponin solution with 5% BSA in PBS for 1 h at room temperature. An anti-cTnT mouse antibody (sc-20025, Santa Cruz, Dallas, USA) and the corresponding isotype control (sc-3878, Santa Cruz) were diluted 1:50 in 0.8% BSA in PBS with 1% saponin and incubated for 30 min at 4° C., respectively. After washing the cells with PBS, cells were incubated with an AF555-conjugated secondary antibody (1:100, A21422, Life Technologies) in 0.8% BSA and 1% saponin in PBS for 1 h at 4° C.

Cells were measured with an Attune acoustic focusing cytometer (Life Technologies) and data was analyzed with the Attune Cytometric software v1.2.5 (Life Technologies). Marker expression was analyzed in a gated population of $10^4$ viable cells.

Statistics:

Statistical analyses were performed with Microsoft Excel software. P values for evaluation of significance between two groups were calculated via two-tailed paired Student's t-test. P-values lower than 0.05 were considered significant in three gradations (* $p<0.001$,  $p<0.01$, * $p<0.05$). $IC_{50}$ uncertainties (standard errors of the estimate, SEE) were calculated using standard errors of regression derived from logarithm-transformed regression analyses of dose response data. Data ratios are stated with propagated uncertainties calculated using standard deviations.

Example 1

Synthesis of the Compounds

The compounds (salans) SM1, SM3, SM4, SM6, SM8-10 were prepared from the starting materials listed in Table 1 as described explicitly for SM6 in: Adao, P; Pessoa, J. C.; Henriques, R. T.; Kuznetsov, M. L.; Avecilla, F.; Maurya, M. R.; Kumar, U.; Correia, I. Synthesis, Characterization, and Application of Vanadium-Salan Complexes in Oxygen Transfer Reactions. Inorg. Chem. 2009, 48, 3542-3561.

The salalens SM2 and SM5 were prepared from the starting materials listed in Table 1 as described in the reference: Berkessel, A., Brandenburg, M., Leitterstorf, E., Frey, J., Lex, J., Schäfer, M. A Practical and Versatile Access to Dihydrosalen (salalen) Ligands: Highly Enantioselective Titanium in situ Catalysis for Asymmetric Epoxidation with Aqueous Hydrogen Peroxide. Adv Synth Catal 2007, 349, 2385-2391.

The bis-salicylic diamide SM7 was prepared as described in the reference: Jimenez, C. A., Belmar, J. B. Synthesis of Highly Hindered Polyanionic Chelating Ligands. Tetrahedron 2005, 61, 3933-3928.

TABLE 1

Structures of the compounds SM1 to SM10, their systematic names, and starting materials used in the synthesis of SM1 to SM10.

| | Formula | compound name | starting compound 1 | starting compound 2 |
|---|---|---|---|---|
| SM1 | | (1S,2S)-N,N'-di[(2-hydroxy-3-phenyl)-benzyl]-1,2-diaminocyclo-hexane | | |
| SM2 | | (1S,2S)-N-[(2-hydroxy-3-phenyl)-benzyl]-N'-[(2-hydroxy-3-phenyl)-benzylidene]-1,2-diaminocyclohexane | | |
| SM3 | | (1R,2R)-N,N'-dimethyl-N,N'-di[(2-hydroxy-3-phenyl)-benzyl]-1,2-diaminocyclohexane | | |
| SM4 | | (1R,2R)-N,N'-di[(2-hydroxy-3-phenyl)-benzyl]-1,2-diaminocyclohexane | | |
| SM5 | | (1R,2R)-N-[(2-hydroxy-3-phenyl)-benzyl]-N'-[(2-hydroxy-3-phenyl)-benzylidene]-1,2-diaminocyclohexane | | |
| SM6 | | (1R,2R)-N,N'-di(2-hydroxybenzyl)-1,2-diaminocyclohexane | | |
| SM7 | | (1R,2R)-N,N'-di[(2-hydroxy-3,5-di-tert.-butyl)benzoyl]-1,2-diaminocyclohexane | | |

TABLE 1-continued

Structures of the compounds SM1 to SM10, their systematic names, and starting materials used in the synthesis of SM1 to SM10.

| | Formula | compound name | starting compound 1 | starting compound 2 |
|---|---|---|---|---|
| SM8 | (1S,2R) cyclohexane with -NH-CH2-(2-hydroxy-3-phenyl-phenyl) groups on both carbons | (1S,2R)-N,N'-di[(2-hydroxy-3-phenyl)-benzyl]-1,2-diaminocyclohexane | (S,R)-1,2-diaminocyclohexane (H2N, NH2) | 2-hydroxy-3-phenyl-benzaldehyde (CHO, OH, Ph) |
| SM9 | (R,R) cyclohexane with N(CH3)-CH2-(2-hydroxy-3,5-di-tert-butylphenyl) groups | (1R,2R)-N,N'-dimethyl-N,N'-di[(2-hydroxy-3,5-di-tert.-butyl)benzyl]-1,2-diaminocyclohexane | (R,R)-N,N'-dimethyl-1,2-diaminocyclohexane | 2-hydroxy-3,5-di-tert-butyl-benzaldehyde |
| SM10 | (R,R) cyclohexane with NH-CH2-(2-hydroxy-3,5-di-tert-butylphenyl) groups | (1R,2R)-N,N'-di[(2-hydroxy-3,5-di-tert.-butyl)benzyl]-1,2-diaminocyclohexane | (R,R)-1,2-diaminocyclohexane | 2-hydroxy-3,5-di-tert-butyl-benzaldehyde |

Example 2

Determination of the Toxicity of Compounds SM1 to SM10 to PSCs

The cytotoxicity of the compounds according to formulas SM1 to SM10 to pluripotent stem cells (PSCs) was determined in a population of murine αPIG-AT25 iPSCs, which were incubated for 48 h with compounds SM1 to SM10 in concentrations of 0.1 µM, 1 µM, 10 µM and 25 µM. Cell culture was performed as described above. Experiments were run in quadruplicate and negative and positive control cells were treated with 0.125% DMSO or 8 µg/ml puromycin, respectively. The cell viability was determined using PrestoBlue cell viability reagent.

FIG. 1 shows the relative viability of the miPSCs after 48 h of treatment with 0.1 µM, 1 µM, 10 µM and 25 µM of the compounds according to formulas SM1 to SM10. As can be seen in FIG. 1, the compounds SM1, SM2, SM4, SM5, SM6 and SM8 had considerable effects on murine αPIG-AT25 iPSCs by killing more than 50% of the cells when applying a concentration as low as 1 µM for 48 hours. After treatment with 10 µM of these compounds, between 82.09±7.96 and 94.1±5.9% of iPSCs were killed which was comparable to the results obtained with 8 µg/ml puromycin that killed 94.3±3.83% of cells. The compounds SM9 and SM10 did not show a concentration dependent effect.

This shows that the compounds SM1, SM2, SM4, SM5, SM6 and SM8 according to formula (1) exhibited good toxicity to miPSCs, while compounds SM3, SM7, SM9 and SM10 of differing substitution pattern did not. Compounds with relevant cytotoxic effects against PSCs had the basic chemical structure of formula (1) in common which was essential for PSC killing, while addition or removal of reactive groups reduced the cytotoxicity.

Example 3

Determination of the Toxicity of the Compounds to Murine Embryonic Stem Cells (mESCs)

To confirm the cytotoxicity of the compounds to PSCs, toxicity test were also run with murine ESC lines αPIG44-D3 and R1, and for comparison with αPIG-AT25 murine iPSC line. The cells were incubated for 48 h with compounds SM1, SM2, SM4, SM5, SM6 and SM8 in concentrations of 0.01 µM and 10 µM. Cell culture was performed as described above. Experiments were run in quadruplicate and negative and positive control cells were treated with 0.05% DMSO or 8 µg/ml puromycin, respectively. Cell viability was determined using PrestoBlue cell viability reagent.

FIG. 2 shows the relative viability of ESCs after 48 h of treatment with 0.01 µM and 10 µM of the compounds. As can be seen in FIG. 2, the elimination of PSCs with 10 µM of compounds SM1, SM2, SM4, SM5, SM6 and SM8 was confirmed for αPIG44-D3 and R1 ESC lines exhibiting an average of 101.53±16.31% of PSCs killed, whereas PSC viability was not affected with 0.01 µM of compounds after 48 h treatment.

This confirms that the compounds SM1, SM2, SM4, SM5, SM6 and SM8 also exhibited toxicity to murine ESCs.

Example 4

Determination of the Half Maximal Inhibitory Concentration ($IC_{50}$) of Compounds in Murine and Human PSCs In order to quantify compound cytotoxicity, dose response assays were performed by treating PSCs with compound concentrations between nontoxic 0.01 μM and PSC-eliminating 10 μM for 48 h. Murine iPSCs αPIG-AT25, embryonic stem cell lines αPIG44-D3 and R1, and human induced pluripotent stem cell (hiPSC) line NP0014-C6 were used. Cell culture and dose response assays were performed as described above.

Regression analyses revealed $IC_{50}$ values in similar ranges between 0.1 and 5 μM for the murine iPSC line, the two murine ESC lines and the human iPSC line. The $IC_{50}$ values compounds SM1, SM2, SM4, SM5, SM6 and SM8 are summarized in the following Table 2. Comparing dose response data derived from human and mouse PSCs after 48 h compound treatment shows that more human induced PSCs survived when exposed to SM2 and SM6 in concentrations between 0.1 and 10 μM resulting in 2.6- to 13.4-fold higher $IC_{50}$ values in human cells, whereas SM8 exerted similar toxicity on human iPSCs and murine PSCs. The compounds SM1, SM4 and SM5 also exerted similar toxicity on human iPSCs and murine PSCs.

TABLE 2

| | $IC_{50}$ of compounds on murine and human PSCs after 48 h of treatment (mean ± SEE; n = 4-20) | | | |
|---|---|---|---|---|
| | αPIG-AT25 miPSC | αPIG-D3 mESC | R1 mESC | hiPSC |
| SM1 | 0.68 ± 0.40 μM | 0.43 ± 0.15 μM | 0.58 ± 0.28 μM | 0.54 ± 0.34 μM |
| SM2 | 1.03 ± 1.09 μM | 0.97 ± 0.58 μM | 0.20 ± 0.17 μM | 2.70 ± 1.25 μM |
| SM4 | 0.60 ± 0.46 μM | 0.63 ± 0.25 μM | 0.60 ± 0.30 μM | 0.36 ± 0.12 μM |
| SM5 | 0.97 ± 0.87 μM | 1.04 ± 0.55 μM | 0.59 ± 0.33 μM | 0.91 ± 0.66 μM |
| SM6 | 0.44 ± 0.39 μM | 0.53 ± 0.23 μM | 0.24 ± 0.18 μM | 1.56 ± 0.71 μM |
| SM8 | 0.78 ± 0.44 μM | 1.10 ± 0.41 μM | 0.26 ± 0.14 μM | 0.29 ± 0.19 μM |

In further experiments, dose-response data from different batches of molecule synthesis validated a stable toxicity against miPSCs using compounds SM2, SM6 and SM8, each of them representing one molecule of an applied stereoisomer group, respectively.

Example 5

Determination of the Selectivity of Compounds to miPSCs and miPSC-Derived CMs The selectivity of compounds was investigated by comparing their cytotoxicity against undifferentiated iPSCs and iPSC-derived CMs. Murine iPSCs αPIG-AT25 were incubated for 48 h with compounds SM1, SM2, SM4, SM5, SM6 and SM8 in concentrations of 0.01 to 10 μM. Cell culture and cardiac differentiation were performed as described above. Experiments were run at least in quadruplicate. The cell viability was determined using PrestoBlue cell viability reagent. FIG. 3a) shows the relative viability of miPSCs and miPSC-derived CMs (miPSC-CM) after 48 h of treatment with compounds. As can be seen in FIG. 3a), a comparison of dose responses determined after 48 h of treatment indicated stable viability of miPSC-derived CMs when applying up to 10 μM of SMs (p>0.05) whereas miPSCs were eliminated. Additionally, microscopic analysis confirmed the presence of intact CM monolayers but absence of miPSCs after 48 h treatment with SM2, SM6 and SM8.

The viability of salicylic diamine-treated CMs was confirmed by 72 h of exposure to concentrations of 0.01 μM, 0.1 μM, 1 μM, 10 μM and 25 μM of compounds SM1, SM2, SM4, SM5, SM6 and SM8. FIG. 3b) shows the relative viability of the αPIG-AT25 miPSC-CMs after 72 h of treatment with the compounds. As can be seen in FIG. 3b), even after 72 h of exposure, only minor decrease of cardiomyocyte viability was observed when treating with 10 μM of SM2 (18.48±7.06%, p<0.01), SM5 (14.06±13.81%, p>0.05) or SM6 (11.04±13.18%; p>0.05) but treatment with stereoisomers SM1, SM4 and SM8 at the same concentration and period of time decreased cardiomyocyte viability in average by 79.79±14.72%.

Since the viability of mouse and human PSC-derived CM monolayers was not affected when they were exposed to concentration ranges that eliminated PSCs, this demonstrates that the cytotoxicity of the compounds was selective against PSCs under experimental conditions specified above.

Example 6

Determination of Side-Effects of Compounds on miPSC-CMs

To further evaluate the toxicity of the compounds on CMs, pure murine αPIG-AT25 iPSC-CM monolayers were treated with 1 and 10 μM of SM2, SM6 and SM8 for 48 hours. Controls were treated with 0.05% DMSO or 75 μg/ml cisplatin, an inducer of apoptotic cardiotoxicity, respectively. Immunocytochemistry was performed as described above Staining of α-actinin and confocal microscopy revealed sarcomeric integrity after treatment with 10 μM compounds, illustrating striation patterns comparable to untreated CMs, whereas application of cisplatin resulted in the degradation of the sarcomere structure. Staining of cleaved caspase-3 showed the presence of apoptotic CMs only when treated with cytotoxic cisplatin but not in salicylic diamine-treated monolayers at both time points, directly after 48 h treatment as well as after 72 h of recovery. These results thus corroborate the cell viability assays described above.

Further, the effect of compound treatment on the CM beating frequency was determined by video imaging of iPSC-CM monolayers after exposure to compounds as described above. FIG. 4 shows the CM beating rates after compound treatment for 48 h and after 72 h of subsequent recovery. As can be taken from FIG. 4, the analysis of the beating CM monolayers showed that the contraction rate of CMs after 48 h treatment with 10 μM of compounds significantly decreased by 61.02±2.67% (SM2, p<0.001), 24.26±15.71% (SM6, p<0.01) and 71.37±26.91% (SM8, p<0.001) compared to average of DMSO-treated control cells. However, after a recovery period of 72 h after compound treatment, the CMs regained contractility levels of control CMs when treated with SM2 and SM6, whereas SM8-treated CMs exhibited even 24.85±6.02% higher beating rates.

This shows that treatment with SM2, SM6 and SM8 neither had durable adverse effects on iPSC-CM sarcomeric integrity nor induced apoptosis in iPSC-CMs after 48 h of treatment. These findings suggest that PSC-derived CMs tolerate the 48 h treatment with compounds using concentrations that eliminated PSCs and that their physiology and functionality are not permanently compromised by the compounds. In any case, the weak side-effects which were detected on iPSC-CMs immediately after exposure to compounds were reversible and CMs mostly regained their properties comparable to non-treated CMs after a recovery period of 72 h.

Example 7

Determination of the Effect of the Compounds on Human iPSCs and Human iPSC-CMs

The selectivity of compound toxicity in the human system was tested on NP0014-6 human induced pluripotent stem cells (hiPSCs) and Cor.4U hiPSC-derived CMs (Axiogenesis, Cologne, Germany).

The human iPSCs were incubated for 48 h with compounds SM2, SM6 and SM8 in concentrations between 0.01 μM and 10 μM. Cell culture and dose response assays were performed as described above. Experiments were run in quadruplicate. Cell viability was determined using PrestoBlue cell viability reagent. The pluripotency of plated hiPSCs was confirmed by immunocytochemical stainings of transcription factors Oct4 and Nanog as well as cell surface antigens SSEA-4 and Tra-1-81, as described above.

FIG. 5a) shows the relative viability of the human iPSCs after 48 h of treatment with the compounds. As can be seen in FIG. 5a), after 48 h of treatment with SM2, SM6 and SM8, the concentrations that fully eliminated hiPSCs were 10 μM for SM2, 3.3 μM for SM6 and 0.5 μM for SM8.

The Cor.4U hiPSC-CMs were incubated for 48 h with 10 μM of SM2, 3.3 μM of SM6 and 0.5 μM of SM8. Negative and positive control cells were treated with DMSO or cisplatin, respectively. Cell culture and dose response assays were performed as described above. Experiments were run in triplicate. Cell viability was determined using PrestoBlue cell viability reagent.

FIG. 5b) shows the relative viability of the human CMs after 48 h of treatment with the compounds. As can be seen in FIG. 5b), the viability of hiPSC-CMs was not affected when they were treated with concentrations of the compounds that were toxic to hiPSCs after treatment for the same period of time. Immunocytochemical staining of α-actinin and DNA damage marker γ-H2AX further demonstrated that the structural integrity of CMs was not compromised by the compounds and that the compounds did not exert DNA-damaging effects on hiPSC-CMs.

These data indicate that the PSC-eliminating and CM-preserving effect of compounds as observed on murine cells also applies to human iPSCs.

Example 8

Determination of the Elimination of Murine PSCs Using Compound SM6 in Pre-Purified Cardiac Clusters of Murine iPSCs In order to verify the applicability of salicylic diamine-mediated selective toxicity for the elimination of PSCs in insufficiently purified cardiac cell aggregates, compound SM6 was applied on pre-purified cardiac clusters which purposely contained a residual fraction of PSCs after cardiogenic differentiation.

Murine αPIG-AT25 iPSCs were differentiated in spinner flasks and pre-purification of CMs with puromycin was initiated on day 9 for a time period of 5 days, as is schematically illustrated in FIG. 6a). Compared to the standard protocol for the selection of miPSC-CMs, the applied concentration of puromycin was reduced from 8 μg/ml to 2 μg/ml in order to preserve a small population of PSCs in the cardiac clusters which were then treated with 1 μM, 5 μM and 10 μM of compound SM6 for 48 hours. Cells were monitored using fluorescence microscopy and video imaging, and it was confirmed that the morphology as well as the contractility of cardiac clusters was not compromised by compound SM6 in any of the applied concentrations.

For quantifying the residual PSCs, the cardiac cluster-derived cells were cultured on MEFs under iPSC conditions to allow PSCs to form colonies which were visualized by crystal violet staining. The pluripotency of grown colonies was confirmed by immunocytochemical stainings for Oct4, at day 7 after plating of CMs from dissociated cardiac clusters on MEF.

FIG. 6b) illustrates the quantification of the developed colonies grown after plating of $2 \times 10^5$ cells derived from the dissociated day 16 cardiac clusters. FIG. 6b) shows that puromycin in a concentration of 8 μg/ml and 1 μM compound SM6 applied for 48 h similarly reduced the number of colonies by 64.87±25.55% and 71.9±21.19%, respectively, compared to the DMSO-treated control group (p<0.001). However, the elimination of colony forming PSCs was not complete and consistent at this concentration of SM6. The application of 5 μM and 10 μM of SM6 for 48 h almost completely prevented the formation of colonies (2.00±2.94 colonies with 5 μM SM6 and 0.37±0.60 colonies with 10 μM SM6 compared to 75.05±27.19 colonies with 0.05% DMSO). This demonstrates an efficient and more consistent toxicity against residual PSCs in cardiac clusters compared to the application of 8 μg/ml puromycin (28.9±23.37 colonies) within the same period of time.

FIG. 6c) illustrates the relative cell yield in cardiac clusters from day 16 of differentiation compared to DMSO-treated control. As can be seen in FIG. 6c), treatment with compound SM6 did not affect the cell yield of day 16 cardiac clusters when compared to the DMSO-treated control group (p>0.05) whereas 8 μg/ml of puromycin reduced the total cell yield significantly by 20.55±14.43% (p<0.01).

Immunostaining of cTnT and flow cytometric analysis confirmed that the PSC-containing population of GFP−/cTnT− non-CMs was diminished by SM6 treatment in a concentration-dependent manner from a 30% fraction in the DMSO-treated control group to a 7% fraction in the group treated with 10 µM SM6 which was comparable to the puromycin-treated group. Coming along with this, the fraction of GFP$^{30}$/cTnT$^+$ CMs raised with increasing concentrations of SM6 to up to 74% of the viable cell population (compared to 52% in the DMSO-treated group).

This demonstrates that SM6, which had lowest side-effects on iPSC-CM monolayers, successfully eliminates PSCs in pre-purified cardiac cell aggregates and preserves morphological and functional properties of CMs which were comparable to untreated controls.

Example 9

Determination of the Elimination of PSCs Using Compound SM6 in Prepurified Cardiac Clusters of Murine ESCs To confirm the PSC-eliminating effect of the compound SM6, pre-purified cardiac clusters derived from transgenic murine ESC line αPIG44-D3 were also treated with SM6. The cells were differentiated in spinner flasks and incubated for 48 h with compound SM6 as described above with the exception that pre-purification was performed with 4 µg/ml of puromycin between day 9 and day 14, as schematically illustrated in FIG. 7a).

It was confirmed that the morphology of ESC-derived clusters after SM6 treatment was similar to those of DMSO or puromycin-treated controls. FIG. 7b) illustrates the quantification of the developed ESC colonies grown after plating 2×10$^5$ cells derived from the dissociated day 16 cardiac clusters in two parallel experiments Exp 1 and Exp 2. It can be taken from FIG. 7b) that 48 h treatment with 5 and 10 µM of SM6 considerably reduced the number of ESC-derived colonies by 93.75±3.45% (5 µM SM6) and 96.23±0.75% (10 µM SM6) compared to DMSO control, whereas the effect of 8 µg/ml puromycin and 1 µM SM6 on colony forming PSCs was minor and inconsistent. Puromycin reduced the number of colonies by 47.83±24.89% and 1 µM SM6 by 20.03±26.95% compared to DMSO control.

FIG. 7c) illustrates the relative cell yield in cardiac clusters from day 16 of differentiation compared to DMSO-treated control. As can be seen in FIG. 7c), the cell yield was reduced in all treated clusters compared to untreated control, but the relative cell yield in the puromycin-treated group was lower (55.85±7.28%) than in the SM6-treated group in which an average yield of 72.87±8.91% compared to the DMSO control was obtained.

This confirms that the compound SM6 also exhibited a capacity to selectively eliminate ESCs in differentiated cardiac clusters in suspension and to improve the final cell yield compared to puromycin-treated control.

Example 10

Determination of the Elimination of Murine iPSCs in Unpurified EBs with SM6

In order to determine whether it is possible to entirely replace puromycin pre-treatment with SM6 and thus circumvent the need for genetic manipulation of PSCs to enable CM selection, the SM6 was supplemented to the differentiation medium of miPSCs from day 9 onwards starting with a concentration of 1 µM which was increased to 5 µM from day 14 until day 16 of differentiation, as is schematically illustrated in FIG. 8a). Control cells received 0.025% DMSO or 8 µg/ml puromycin during this time period (day 9 to day 16 of differentiation).

Immunostaining of cTnT showed that the DMSO-treated cell aggregates contained GFP$^+$/cTnT$^+$ CMs as well as GFP$^-$/cTnT$^+$ CMs, while after purification with puromycin almost all GFP$^-$ cells including the fraction of GFP$^-$/cTnT$^+$ CMs were eliminated and only GFP$^+$/cTnT$^+$ CMs remained due to the coupled expression of puromycin resistance and GFP under the cardiac αMHC promoter. Treatment with SM6, however, preserved the GFP$^-$/cTnT$^+$ fraction of CMs which was approximately of the same size as the GFP$^{+1}$/cTnT$^+$ CM population, and decreased the content of GFP$^-$/cTnT$^-$ non-CMs. Quantification of the cTnT$^+$ CM population based on flow cytometric data of independent experiments revealed that both puromycin and SM6 treatment enhanced the CM purity compared to the DMSO-treated control cells by an average of 3.08±1.42-fold increase in puromycin-treated group and 2.56±1.25-fold increase in SM6-treated group. However, the cTnT$^+$ CM population was lesser in SM6-treated cell aggregates (77.57±12.26%) compared to the puromycin-treated cells (93.26±3.05%) which was assumed to be due to the fraction of cTnT$^-$non-CMs detectable in this group, which was most likely comprised of other differentiated cell types and did not contain undifferentiated PSC because they were shown above to be eliminated under these culture conditions.

FIG. 8b) illustrates the relative total cell yield (left hand panel) and CM yield (right hand panel) in cardiac clusters from day 16 of differentiation compared to DMSO-treated control. As can be seen in the left bar graph of FIG. 8b), CM purification with puromycin or SM6 resulted in a strong decrease of the total cell yield after dissociation of cell aggregates: the cell yield was reduced by 92.17±3.53% in puromycin-treated aggregates and by 56.6±10.44% in SM6-treated aggregates relative to DMSO control. Altogether, however, the treatment with SM6 resulted in a 2.72±1.61-fold higher yield of cTnT$^+$ CMs compared to the treatment with puromycin (p<0.01), as can be seen in the right bar graph of FIG. 8b). This effect was caused by the preservation of GFP$^-$/cTnT$^+$ CMs in the SM6-treated group. In three out of five experiments the CM yield was even 31-86% higher compared to the DMSO-treated control group as can be seen in the right bar graph of FIG. 8b). This finding suggests that CMs proliferate under SM6 conditions.

As was determined by colony formation assay, the treatment with SM6 lead to a reduction of contaminating colony-forming PSCs by 98.88±1.04% which was comparable to the standard procedure using puromycin which showed a 97.55±4.02% decrease of colony numbers. Cardiomyocyte integrity as well as the preservation of GFP-negative CMs after SM6 treatment was confirmed by immunocytochemical staining of α-actinin in day 16 iPSC-CMs which showed the presence of α-actinin/GFP-double positive and α-actinin-positive but GFP-negative cells exhibiting the same striation patterns as CMs in the DMSO- or puromycin-treated control groups, as well as a few α-actinin-negative non-CMs.

These data show that the small molecule based elimination of PSCs using SM6 has significant advantage over genetic selection because it most likely preserves the entire CM population independently of subtype and results in higher CM yields than the transgenic approach using puromycin.

Example 11

Determination of the Half Maximal Inhibitory Concentration (IC$_{50}$) of Stereoisomers and Derivatives of Compound SM6

Since compound SM6 possessed the lowest IC$_{50}$ value against miPSCs and exerted least side effects on miPSC- CMs, additional analyses of stereoisomers and SM6-based molecule structures were performed. Dose response assays were performed by treating αPIG-AT25 murine iPSCs with compound concentrations between nontoxic 0.01 μM and PSC-eliminating 10 μM for 48 h. Experiments were run in quadruplicate. Cell culture and dose response assays were performed as described above.

A comparison of the SM6 stereoisomers revealed a slightly increased toxicity of the R,R isomer compared to the S,S and S,R isomers.

Example for Comparison 12

Determination of Cytotoxic Effects on Murine PSCs of PluriSIn #1

For comparison with SM6, the PSC-eliminating effects of PluriSIn #1 were determined using the experimental conditions as for the compounds.

Murine αPIG-AT25 iPSCs, αPIG44-D3 ESCs and R1 ESCs were incubated with 40 μM PluriSIn #1 (Sigma-Aldrich, catalog number SML0682) for 72 h. Cell culture was performed as described above for determination of the compounds. Experiments were run in quadruplicate and negative and positive control cells were treated with 0.08% DMSO or 8 μg/ml puromycin, respectively. The cell viability was determined using PrestoBlue cell viability reagent. It was seen that while 8 μg/ml puromycin killed 96.4±2.83% of PSCs ($p<0.001$), PluriSIn #1 reduced the cell viability of murine αPIG-AT25 iPSCs, αPIG44-D3 ESCs and R1 ESCs on average by only 51.32±10.86%. PSCs were still detected by microscopic analysis after 3 days of treatment with 40 μM of PluriSIn #1, which is double the concentration than that reported to be toxic for human PSCs.

This shows that concentrations of 1 μM, 10 μM or 25 μM of the compounds SM1, SM2, SM4, SM5, SM6 and SM8 exhibited higher toxicity to murine iPSCs than 40 μM of PluriSIn #1 under the tested conditions.

In summary, the examples show a selective toxicity of the compounds of formula (1) to murine and human iPSCs but not to murine and human iPSC-CMs. The compounds SM2, SM6 and SM8 eliminated PSCs in concentrations that were not toxic to PSC-CMs. The 48 hour treatment with compounds at those concentrations had minor effects on the sarcomeric morphology of CM monolayers and did not induce apoptosis or DNA damage in these cells. Particularly SM6 provides efficient killing of PSCs in a PSC-derived CM population while exerting no or tolerable and reversible side-effects on CMs.

The chemical ablation of PSCs using the compounds provides a simple and clinically most versatile approach for the elimination of tumorigenic PSCs. The application is scalable and the ease of handling as well as the absence of genetic manipulation of cells means considerable advantages for GMP-grade CM manufacturing in order to supply sufficient numbers of safe CMs as required for the implementation of PSC-CMs in in vitro applications and regenerative medicine.

Example 13

Synthesis of Compounds SM20, SM21, SM22 and SM23

The compounds SM20, SM21, SM22 and SM23 were prepared from the starting materials listed in Table 3 as described explicitly for SM6 in example 1.

TABLE 3

Structures of the compounds SM20, SM21, SM22 and SM23, their systematic names, and starting materials used in the synthesis of SM20, SM21, SM22 and SM23.

| | Formula | compound name | starting compound 1 | starting compound 2 |
|---|---|---|---|---|
| SM20 | [structure] | (1R,2R)-N,N'-di[(2-hydroxy-3-pentafluorophenyl)-benzyl]-1,2-diaminocyclohexane | (R),(R)-1,2-diaminocyclohexane | 2-hydroxy-3-C$_6$F$_5$-benzaldehyde |
| SM21 | [structure] | (1R,2R)-N,N'-di[(2-indolyl)methyl]-1,2-diaminocyclohexane | (R),(R)-1,2-diaminocyclohexane | indole-2-CHO |
| SM22 | [structure] | (1R,2R)-N,N'-di[(6-indolyl)methyl]-1,2-diaminocyclohexane | (R),(R)-1,2-diaminocyclohexane | indole-7-CHO |

TABLE 3-continued

Structures of the compounds SM20, SM21, SM22 and SM23, their systematic names, and starting materials used in the synthesis of SM20, SM21, SM22 and SM23.

| | Formula | compound name | starting compound 1 | starting compound 2 |
|---|---|---|---|---|
| SM23 | | (1R,2R)-N,N'-di([2-hydroxy-3-(2-thienyl)]-benzyl)-1,2-diaminocyclohexane | (R),(R) H$_2$N NH$_2$ cyclohexane | CHO, OH, phenyl-thiophene |

Example 14

Determination of the Toxicity of Compounds SM20, SM21, SM22 and SM23

The cytotoxicity of the compounds according to formulas SM20, SM21, SM22 and SM23 to pluripotent stem cells (PSCs) was determined in a population of murine αPIG-AT25 iPSCs, which were incubated for 48 h with compounds SM20, SM21, SM22 and SM23 in concentrations of 0.1 μM, 1 μM, 10 μM and 25 μM. Cell culture was performed as described in example 2. Experiments were run in quadruplicate and negative and positive control cells were treated with 0.125% DMSO or 0.1 μM, 1 μM, 10 μM and 25 μM of the compound SM6, respectively. The cell viability was determined using PrestoBlue cell viability reagent.

FIG. 9 shows the relative viability of the miPSCs after 48 h of treatment with 0.1 μM, 1 μM, 10 μM and 25 μM of the compounds according to formulas SM20, SM21, SM22 and SM23. As can be seen in FIG. 9, the compounds had considerable effects on murine αPIG-AT25 iPSCs by killing more than 95% of the cells when applying a concentration as low as 1 μM for compounds SM20 and SM24 and of 10 μM for compounds SM22 and SM23 for 48 hours. After treatment with 10 μM of these compounds all iPSCs were killed which was comparable to the results obtained with 10 μM of SM6. This shows that also the compounds SM20, SM21, SM22 and SM23 exhibited good toxicity to miPSCs.

Example 15

Determination of the Toxicity of the Compounds SM20, SM21, SM22 and SM23 on Human iPSC-Derived Neural Progenitor Cells (NPCs)

To confirm the cytotoxicity of the compounds to PSCs, toxicity tests were also run with human neural progenitor cells (passage 20) derived from the human iPSC line Royan-hiPSC4 (RSCB0082). The cells were incubated for 24 h, 48 h and 72 h with compounds SM20, SM21, SM22 and SM23 in concentrations of 1 μM, 3 μM, 10 μM and 25 μM. Cell culture was performed as described above except that Koch medium was used. Experiments were run in quadruplicate and negative and positive control cells were treated with 0.001% DMSO or 0.1 μM, 1 μM, 10 μM and 25 μM of SM6, respectively. Cell viability was determined using PrestoBlue cell viability reagent.

FIGS. 10a, 10b and 10c show the relative viability of human NPCs after, respectively, 24 h, 48 h or 72 h of treatment with 1 μM, 3 μM, 10 μM or 25 μM of the compounds. As can be seen in FIG. 10, all tested compounds exhibited significant toxicity against hiPSC-derived NPCs killing about 60-90% of cells already after 24 h of treatment when used at the concentration of 3 μM. Compounds SM6, SM21 and SM22 seemed to be somewhat less toxic than SM20 and SM23 because even after 72 h of treatment the former compounds were not able to kill more than 10-20% of cells at 1 μM concentration, while the latter eliminated all cells at the same dose.

This confirms that, albeit at different extents, the compounds SM6, SM20, SM21, SM22 and SM23 also exhibited toxicity to human NPCs. This indicates that besides iPSCs their toxicity spectrum also involves NPCs further emphasizing their special mechanism of action that is not detrimental to iPSC-derived CMs at concentrations that are killing iPSCs and NPCs.

The invention claimed is:

1. A method of reducing the number or percentage of pluripotent stem cells or of enriching differentiating or differentiated cells in a cell population comprising pluripotent stem cells and differentiating cells or differentiated cells derived from the pluripotent stem cells, the method comprising the step of contacting the cell population with a compound according to the following general formula (1) and/or racemates, enantiomers, stereoisomers, solvates, hydrates or salts thereof:

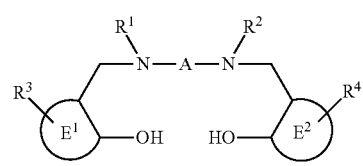

(1)

wherein:
R$^1$, R$^2$ the same or independent from each other are hydrogen or represent a double bond from the nitrogen atom to the adjacent non-cyclic carbon atom;
R$^3$, R$^4$ are the same or independently from each other selected from the group comprising hydrogen, linear or branched C$_1$-C$_8$-alkyl, C$_2$-C$_8$-alkenyl, C$_3$-C$_8$-cycloalkyl, C$_6$-C$_{10}$-aryl, C$_1$-C$_8$-alkoxy and halogen;
E$^1$, E$^2$ are the same or independent from each other a 5- or 6-membered aromatic or heteroaromatic ring selected from the group comprising thiophenyl, pyrrolyl, pyridyl and phenyl;

A is selected from the group of structural elements of formulas (2) and (3):

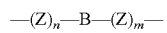  (2)

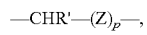  (3)

wherein:
B is selected from the group comprising $C_3$-$C_8$-cycloalkyl, $C_3$-$C_8$-heterocycloalkyl, $C_6$-$C_{10}$-aryl and $C_5$-$C_{10}$-heteroaryl;
Z is the same or independently from each other selected from the group comprising —$CH_2$—, —CHR'—, O, S, NH, NR';
R' is the same or independently from each other selected from the group comprising hydrogen, $C_1$-$C_8$-alkyl, $C_2$-$C_8$-alkenyl, $C_3$-$C_8$-cycloalkyl and $C_6$-$C_{10}$-aryl;
n, m are the same or independent from each other 0, 1 or 2;
p is 1, 2, 3, 4, or 5; or contacting the cell population with a compound of formula (6)

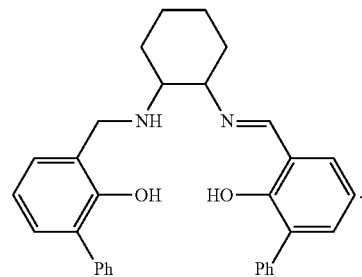  (6)

2. The method according to claim 1, wherein the compound is a compound according to the following general formula (4) and/or racemates, enantiomers, stereoisomers, solvates, hydrates or salts thereof:

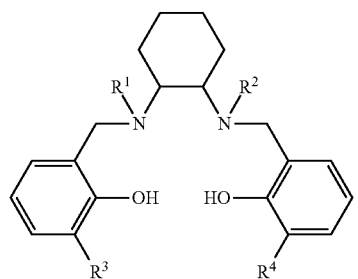  (4)

wherein:
$R^1$, $R^2$ the same or independent from each other are hydrogen or represent a double bond from the nitrogen atom to the adjacent non-cyclic carbon atom; and
$R^3$, $R^4$ are the same or independently from each other selected from the group comprising hydrogen, linear or branched $C_1$-$C_8$-alkyl, $C_2$-$C_8$-alkenyl, $C_3$-$C_8$-cycloalkyl and $C_6$-$C_{10}$-aryl.

3. The method according to claim 1, wherein the compound is selected from the group of compounds according to formulas (SM2), (SM6) and (SM8) as given as follows:

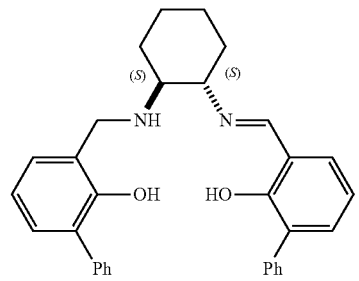  (SM2)

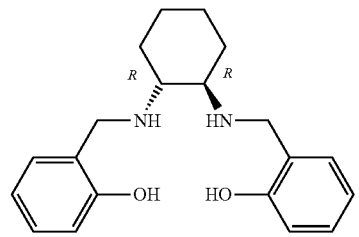  (SM6)

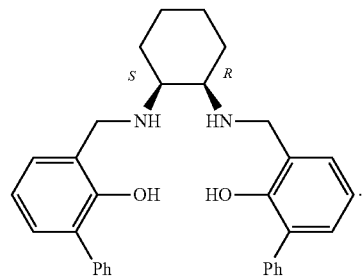  (SM8)

4. The method of claim 1, wherein the step of contacting the cell population with a compound comprises incubating the cell population in a cell culture medium containing a compound according to general formula (1).

5. The method of claim 1, wherein the differentiating or differentiated cells are cardiomyocytes.

6. The method of claim 1, wherein the pluripotent stem cells are induced pluripotent stem cells or embryonic stem cells.

7. The method of claim 1, wherein the pluripotent stem cells are human cells.

8. The method of claim 1, wherein the method is for enriching cardiomyocyte subtypes selected from the group consisting of atrial, ventricular and pacemaker cells.

9. The method of claim 1, wherein the method is a non-transgenic and/or resistance or selection marker-free method of enriching cardiomyocytes.

10. A composition comprising pluripotent stem cells and differentiating cells or differentiated cells derived from the pluripotent stem cells, and a compound according to the general formula (1) and/or racemates, enantiomers, stereoisomers, solvates, hydrates or salts thereof:

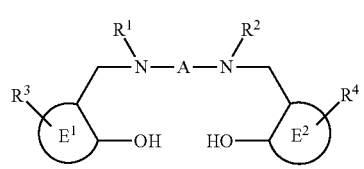  (I)

wherein:
R$^1$, R$^2$ the same or independent from each other are hydrogen or represent a double bond from the nitrogen atom to the adjacent non-cyclic carbon atom;
R$^3$, R$^4$ are the same or independently from each other selected from the group comprising hydrogen, linear or branched C$_1$-C$_8$-alkyl, C$_2$-C$_8$-alkenyl, C$_3$-C$_8$-cycloalkyl, C$_6$-C$_{10}$-aryl, C$_1$-C$_8$-alkoxy and halogen;
E$^1$, E$^2$ are the same or independent from each other a 5- or 6-membered aromatic or heteroaromatic ring selected from the group comprising thiophenyl, pyrrolyl, pyridyl and phenyl;
A is selected from the group of structural elements of formulas (2) and (3):

(2)

(3)

wherein:
B is selected from the group comprising C$_3$-C$_8$-cycloalkyl, C$_3$-C$_8$-heterocycloalkyl, C$_6$-C$_{10}$-aryl and C$_5$-C$_{10}$-heteroaryl;
Z is the same or independently from each other selected from the group comprising —CH$_2$—, —CHR'—, O, S, NH, NR';
R' is the same or independently from each other selected from the group comprising hydrogen, C$_1$-C$_8$-alkyl, C$_2$-C$_8$-alkenyl, C$_3$-C$_8$-cycloalkyl and C$_6$-C$_{10}$-aryl;
n, m are the same or independent from each other 0, 1 or 2;
p is 1, 2, 3, 4, or 5; or a compound according to formula (6)

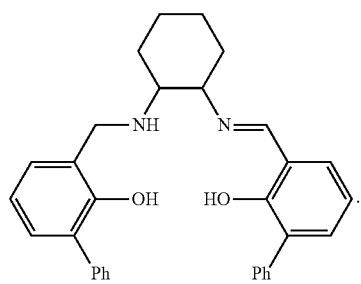
(6)

11. The composition according to claim 10, wherein the compound is a compound according to general formula (4) or formula (6).

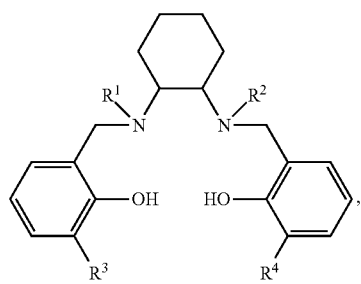
(4)

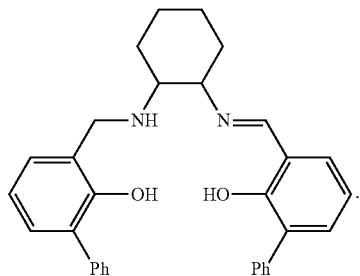
(6)

12. The composition of claim 10, wherein the compound is a compound according to the following general formula (4) and/or racemates, enantiomers, stereoisomers, solvates, hydrates or salts thereof:

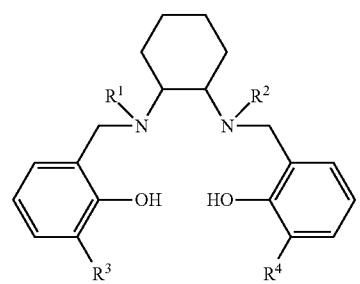
(4)

wherein:
R$^1$, R$^2$ the same or independent from each other are hydrogen or represent a double bond from the nitrogen atom to the adjacent non-cyclic carbon atom; and
R$^3$, R$^4$ are the same or independently from each other selected from the group comprising hydrogen, linear or branched C$_1$-C$_8$-alkyl, C$_2$-C$_8$-alkenyl, C$_3$-C$_8$-cycloalkyl and C$_6$-C$_{10}$-aryl.

13. The composition of claim 11, wherein the compound is selected from the group consisting of compounds according to formulas (SM2), (SM6) and (SM8) as given as follows:

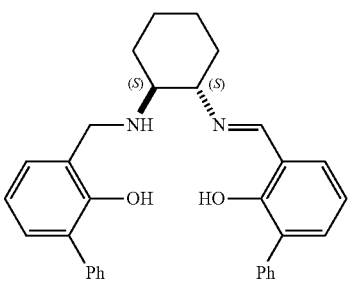
(SM2)

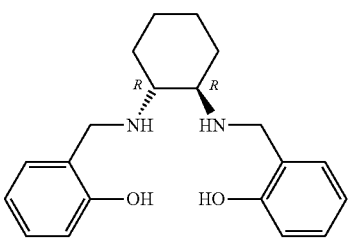
(SM6)

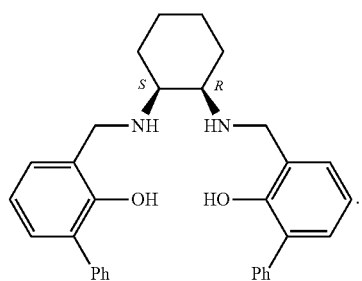
(SM8)

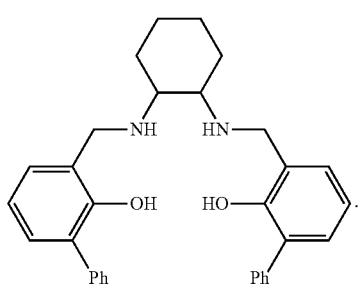
(7)

14. The composition of claim 10, wherein the pluripotent stem cells are induced pluripotent stem cells or embryonic stem cells.

15. The composition of claim 10, wherein the pluripotent stem cells are human cells.

16. The method of claim 4, wherein the compound is a compound of formulas (4) to (7)

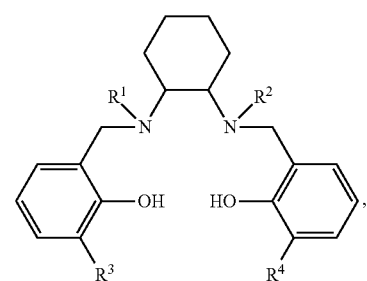
(4)

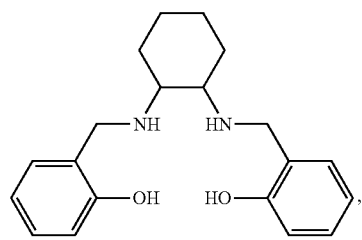
(5)

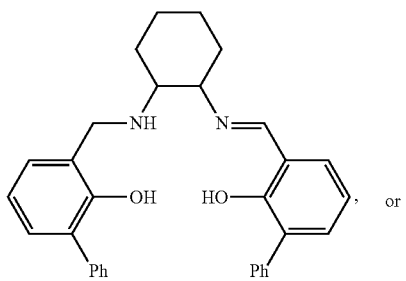
(6)

17. The method of claim 4, wherein the compound is a compound of formulas (SM6), (SM2) and (SM8) in a range from ≥0.01 µM to ≤100 µM, wherein the formulas have the structure

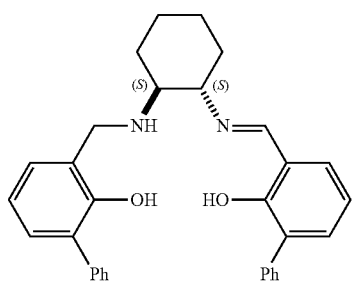
(SM2)

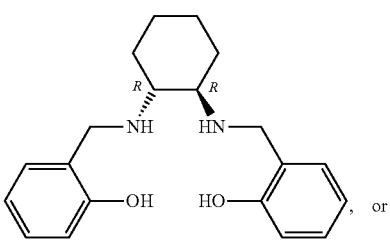
(SM6)

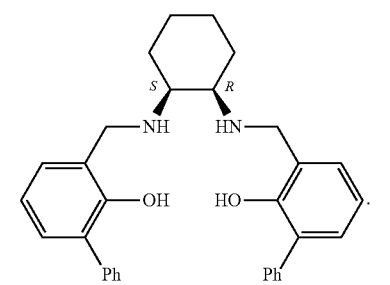
(SM8)

18. The method of claim 4, wherein the compound is in a range from ≥0.05 µM to ≤10 µM.

19. The method of claim 4, wherein the compound is in a range from ≥0.05 µM to ≤2 µM.

* * * * *